United States Patent
Patriciu et al.

(10) Patent No.: US 11,911,207 B2
(45) Date of Patent: Feb. 27, 2024

(54) X-RAY RING MARKERS FOR X-RAY CALIBRATION

(71) Applicant: KONINKLIJKE PHILIPS N.V., Eindhoven (NL)

(72) Inventors: Alexandru Patriciu, Belmont, MA (US); Alyssa Torjesen, Charlestown, MA (US); Molly Lara Flexman, Melrose, MA (US); Ashish Sattyavrat Panse, Burlington, MA (US); Marcin Arkadiusz Balicki, Cambridge, MA (US); Ronaldus Frederik Johannes Holthuizen, Culemborg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 325 days.

(21) Appl. No.: 17/423,921

(22) PCT Filed: Mar. 25, 2020

(86) PCT No.: PCT/EP2020/058278
§ 371 (c)(1),
(2) Date: Jul. 19, 2021

(87) PCT Pub. No.: WO2020/193598
PCT Pub. Date: Oct. 1, 2020

(65) Prior Publication Data
US 2022/0087633 A1    Mar. 24, 2022

Related U.S. Application Data

(60) Provisional application No. 62/823,190, filed on Mar. 25, 2019.

(51) Int. Cl.
A61B 6/00    (2006.01)
A61B 6/08    (2006.01)

(52) U.S. Cl.
CPC ............ *A61B 6/584* (2013.01); *A61B 6/4441* (2013.01); *A61B 6/08* (2013.01); *A61B 6/587* (2013.01)

(58) Field of Classification Search
CPC ..................................................... A61B 6/584
See application file for complete search history.

(56) References Cited

U.S. PATENT DOCUMENTS 5,442,674 A    8/1995  Picard
5,822,396 A *  10/1998 Navab .................... A61B 6/583
                                                    378/207

(Continued)

OTHER PUBLICATIONS

International Search Report and Written Opinion of PCT/EP2020/058278, dated Jun. 3, 2020.

(Continued)

*Primary Examiner* — Chih-Cheng Kao

(57) ABSTRACT

Various embodiments of the present disclosure include a C-arm registration system employing a controller (70) for registering a C-arm (60) to a X-ray ring marker (20). The X-ray ring marker (20) includes a coaxial construction of a chirp ring (40) and a centric ring (50) on an annular base (30). In operation, the controller (70) acquires a baseline X-ray image illustrative of the X-ray ring marker (20) within a baseline X-ray projection by the C-arm (60) at a baseline imaging pose, derives baseline position parameters of the X-ray ring marker (20) within the baseline X-ray projection as a function of an illustration of the centric ring (50) within the baseline X-ray image, and derives a baseline twist parameter of the X-ray ring marker (20) within the baseline X-ray projection as a function of the baseline position parameters and of an illustration of the chirp ring (40) within the baseline X-ray image.

20 Claims, 18 Drawing Sheets

(56) References Cited

U.S. PATENT DOCUMENTS

| | | | |
|---|---|---|---|
| 5,835,563 A * | 11/1998 | Navab | A61B 6/12 |
| | | | 378/207 |
| 2001/0022834 A1 | 9/2001 | Graumann | |
| 2016/0106338 A1* | 4/2016 | Kruger | G06T 11/00 |
| | | | 345/633 |

OTHER PUBLICATIONS

Steger, Teena et al "Marker Detection Evaluation by Phantom and Cadaver Experiments for C-arm Pose Estimation Pattern", Proceeding of SPIE, Medical Imaging 2013, vol. 8671.

* cited by examiner

X-RAY RING MARKERS FOR X-RAY CALIBRATION

CROSS-REFERENCE TO PRIOR APPLICATIONS

This application is the U.S. National Phase application under 35 U.S.C. § 371 of International Application No. PCT/EP2020/058278, filed on Mar. 25, 2020, which claims the benefit of U.S. Provisional Patent Application Ser. No. 62/823,190, filed Mar. 25, 2019. These applications are hereby incorporated by reference herein.

FIELD OF THE INVENTION

The present disclosure generally relates to X-ray calibration. The present disclosure specifically relates to an imaging of a X-ray ring marker for X-ray calibration.

BACKGROUND OF THE INVENTION

X-ray C-Arm systems are frequently used in minimally invasive surgical procedures (e.g., orthopedic procedures, vascular interventions, etc.) for enabling surgeons to see inside a patient body by taking X-ray images from arbitrary directions. More particularly, a mobile C-Arm usually has wheels to provide mobility around the room and once positioned, the mobile C-Arm allows the user to adjust the position of the C-Arm in five (5) directions. While this provides flexibility in the execution of minimally invasive surgical procedures, the exact position and angle of the X-ray projection is not known. This precludes the user from employing advanced tools including making true three-dimensional ("3D") measurements, large field of view imaging, dynamic overlay of pre-operative or intraoperative information, and target localization for image guided intervention. Thus, after a positioning of the mobile C-Arm with respect to the patient body, there has been a need to compute a pose of the X-ray projection with respect to a fixed coordinate system, which is conventionally called C-Arm Registration. Specifically, a mobile C-Arm position is computed with respect to a fixed coordinate system and described by a homogeneous transformation composed of a translation vector ($t \in R^3$) and a rotation matrix ($R \in SO(3)$). Therefore, the task has been to compute the pair (t, R) that accurately describes the position of the mobile C-Arm with respect to the fixed coordinate system.

One historic approach for solving the C-Arm Registration required an installation of hardware on the C-Arm (e.g., optical tracking markers, inertial markers, etc.). This approach requires the addition of multiple components to the room and often negatively impacts the workflow for the procedure.

A current practice for C-Arm Registration is to provide a marker having a fixed position in the operating space (e.g., a marker attached to a robot or an operating table), and to generate a X-ray image of features of the marker to perform the C-Arm Registration (e.g., steel balls or features of a known geometry). For such markers, there are cost-benefit tradeoffs with respect to a required registration accuracy, the number of opaque features on the marker, size of the marker, impact to the workflow, and impact to the x-ray image.

SUMMARY OF THE INVENTION

While known C-Arm Registration methods have proven to be beneficial, there remains a need for improved techniques for providing accurate and reliable C-Arm Registration, particularly for mobile C-Arms.

The present disclosure teaches a X-ray ring marker that includes a centric ring serving as a discrete feature and a chirp ring serving as a continuous feature, whereby the discrete/continuous features of the X-ray ring marker provide a more accurate and reliable C-arm to X-ray ring marker registration that facilitates a robust computation of imaging poses of a C-Arm.

Specifically, a position and a twist of the X-ray ring marker in a X-ray projection by a X-ray source of the C-Arm to a X-ray detector of the C-arm as defined by registration parameters derived from the centric ring and the chirp ring represent a rigid body transformation from a C-Arm attached coordinate system to a X-ray ring marker attached coordinate system.

A first phase of the C-arm to X-ray ring marker registration involves a generation of baseline position/twist parameters associated with a baseline imaging pose of the C-arm. A second phase of the C-arm registration involves a movement of the C-arm to a target imaging pose (e.g., a vertical translation, a horizontal translation and/or a rotation of the C-arm) and a generation of target position/twist parameters associated with a target imaging pose of the C-arm. These registration parameters collectively facilitate implementation of various intervention steps including, but not limited, a distance measurement between landmarks in the baseline/target images, a computation of three-dimensional angles between lines in the baseline/target images and three-dimensional reconstruction of linear or tree-like structures from the baseline/target images.

One embodiment of the present disclosure is an C-Arm registration system employing a C-Arm registration controller for registering a C-Arm to a X-ray ring marker. The X-ring marker includes a coaxial construction of a chirp ring and a centric ring on an annular base.

For registering the C-arm to the X-ray ring marker at a baseline imaging pose, a C-Arm registration controller is configured to (1) acquire a baseline X-ray image illustrative of the X-ray ring marker within a baseline X-ray projection by C-arm at the baseline imaging pose, (2) derive baseline position parameters as a function of a delineation of the centric ring within the baseline X-ray image, the baseline position parameters being definitive of a position of the X-ray ring marker within the baseline X-ray projection and (3) derive a baseline twist parameter as a function of the baseline position parameters and a delineation of the chirp ring within the baseline X-ray image, the baseline twist parameter being definitive of a twist of the X-ray ring marker within the baseline X-ray projection.

For registering the C-arm to the X-ray ring marker at a target imaging pose, the C-Arm registration controller is may be further configured to (1) acquire a target X-ray image illustrative of the X-ray ring marker within a target X-ray projection by C-arm as the target imaging pose, (2) derive target position parameters as a function of a delineation of the centric ring within the target X-ray image, the target position parameters being definitive of a position of the X-ray ring marker within the target X-ray projection, and (3) derive a target twist parameter as a function of the target position parameters and a delineation of the chirp ring within the target X-ray image, the target twist parameter being definitive of a twist of the X-ray ring marker within the target X-ray projection.

For facilitating an execution of an intervention procedure, the C-Arm registration controller may be further configured to implement an intervention step based on a landmark as illustrated in the baseline X-ray image and the target X-ray image as a function of the baseline position parameters, the baseline twist parameter, the target position parameters and the target twist parameter.

One embodiment of the C-Arm registration controller, for registering the C-arm to the X-ray ring marker at a baseline imaging pose, employs a non-transitory machine-readable storage medium encoded with instructions for execution by one or more processors to (1) acquire a baseline X-ray image illustrative of the X-ray ring marker within the baseline X-ray projection by the C-Arm at the baseline imaging pose, (2) derive baseline position parameters as a function of a delineation of the centric ring within the baseline X-ray image, the baseline position parameters being definitive of a position of the X-ray ring marker within the baseline X-ray projection and (3) derive a baseline twist parameter as a function of the baseline position parameters and a delineation of the chirp ring within the baseline X-ray image, the baseline twist parameter being definitive of a twist of the X-ray ring marker within the baseline X-ray projection.

For registering the C-arm to the X-ray ring marker at a target imaging pose, the non-transitory machine-readable storage medium may be further encoded with instructions for execution by the processor(s) to (1) acquire a target X-ray image illustrative of the X-ray ring marker within a target X-ray projection by C-arm as the target imaging pose, (2) derive target position parameters as a function of a delineation of the centric ring within the target X-ray image, the target position parameters being definitive of a position of the X-ray ring marker within the target X-ray projection, and (3) derive a target twist parameter as a function of the target position parameters and a delineation of the chirp ring within the target X-ray image, the target twist parameter being definitive of a twist of the X-ray ring marker within the target X-ray projection.

For facilitating an execution of an intervention procedure, the non-transitory machine-readable storage medium may be further encoded with instructions for execution by the processor(s) to implement an intervention step based on a landmark as illustrated in the baseline X-ray image and the target X-ray image as a function of the baseline position parameters, the baseline twist parameter, the target position parameters and the target twist parameter.

Another embodiment of the present disclosure is an C-Arm registration method executable by the C-Arm registration controller. In operation, the C-Arm registration controller (1) acquires a baseline X-ray image illustrative of the X-ray ring marker within a baseline X-ray projection by the C-Arm at a base line pose, (2) derives baseline position parameters as a function of a delineation of the centric ring within the baseline X-ray image, the baseline position parameters being definitive of a position of the X-ray ring marker within the baseline X-ray projection and (3) derives a baseline twist parameter as a function of the baseline position parameters and a delineation of the chirp ring within the baseline X-ray image, the baseline twist parameter being definitive of a twist of the X-ray ring marker within the baseline X-ray projection.

For registering the C-arm to the X-ray ring marker at a target imaging pose, in operation the C-Arm registration controller may (1) acquire a target X-ray image illustrative of the X-ray ring marker within a target X-ray projection by C-arm as the target imaging pose, (2) derive target position parameters as a function of a delineation of the centric ring within the target X-ray image, the target position parameters being definitive of a position of the X-ray ring marker within the target X-ray projection, and (3) derive a target twist parameter as a function of the target position parameters and a delineation of the chirp ring within the target X-ray image, the target twist parameter being definitive of a twist of the X-ray ring marker within the target X-ray projection.

For facilitating an execution of an intervention procedure, in operation the C-Arm registration controller may implement an intervention step based on a landmark as illustrated in the baseline X-ray image and the target X-ray image as a function of the baseline position parameters, the baseline twist parameter, the target position parameters and the target twist parameter.

For purposes of the description and claims of the present disclosure:

(1) terms of the art including, but not limited to, "marker", "X-ray image", "C-Arm", "X-ray source", "X-ray detector", "X-ray projection", "registration", "intervention", "landmark", "chirp", "annular", "parameter", "parametrize" and "derive" are to be interpreted as known in the art of the present disclosure and as exemplary described in the present disclosure;

(2) the term "X-ray ring marker" broadly encompasses, as exemplary shown in the present disclosure and hereinafter conceived, a coaxial construction of a centric ring and a chirp ring;

(3) the term "centric ring" broadly encompasses, as exemplary shown in the present disclosure and hereinafter conceived, a X-ray imageable annular structure embodying a center of the X-ray ring marker, such as, for example, a X-ray imageable circular shaped ring or a X-ray imageable elliptical shaped ring embodying a center a X-ray ring marker defined by a spatial arrangement of protrusions formed in a X-ray imageable annular base, a spatial arrangement of indentations formed in the a X-ray imageable annular base, and/or a spatial arrangement of X-ray imageable objects disposed onto/into an annular base (e.g., cooper balls, brass balls, etc.);

(4) the term "chirp ring" broadly encompasses, as exemplary shown in the present disclosure and hereinafter conceived, a X-ray imageable annular structure embodying a chirp signal, such as, for example, a X-ray imageable circular shaped ring or a X-ray imageable elliptical shaped ring embodying a chirp signal defined by a spatial arrangement of protrusions formed in a X-ray imageable annular base, a spatial arrangement of indentations formed in a X-ray imageable annular base, and/or a spatial arrangement of X-ray imageable objects disposed onto/into an annular base (e.g., cooper balls, brass balls, etc.);

(5) the term "coaxial construction" broadly encompasses a permanent formation/disposal or a transient disposal of the centric ring and the chirp ring on the annular base including a concentric axial alignment or an eccentric axial alignment of the centers of the centric ring and the chirp ring;

(6) the terms "baseline" and "target" are used in the present disclosure as labels for distinguishing various X-ray images, X-ray projections and imaging poses and do not limit the scope of X-ray images, X-ray projections and imaging poses.

(7) the term "controller" broadly encompasses all structural configurations, as understood in the art of the present disclosure and as exemplary described in the present disclosure, of main circuit board or integrated circuit for controlling an application of various aspects of the present disclosure as exemplary described in the present disclosure. The structural configuration of the controller may include, but is not limited to, processor(s), computer-usable/computer readable storage medium(s), an operating system, application module(s), peripheral device controller(s), slot(s) and port(s). A controller may be housed within or linked to a workstation. Examples of a "workstation" include, but are not limited to, an assembly of one or more computing devices, a display/monitor, and one or more input devices (e.g., a keyboard, joysticks and mouse) in the form of a standalone computing system, a client computer of a server system, a desktop or a tablet;

(8) the term "application module" broadly encompasses an application incorporated within or accessible by a controller consisting of an electronic circuit (e.g., electronic components and/or hardware) and/or an executable program (e.g., executable software stored on non-transitory computer readable medium(s) and/or firmware) for executing a specific application;

(9) the phrase "as a function of" broadly encompasses a mathematical relationship and/or a non-mathematical relationship between input variables and output variables of an application module whereby each input variable or combination of input variables of the application module derives a single output variable; and

(10) the terms "data" and "signal" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various aspects of the present disclosure as subsequently described in the present disclosure. Data/signal communication components of the present disclosure may involve any communication method as known in the art of the present disclosure including, but not limited to, data/signal transmission/reception over any type of wired or wireless datalink/signal link and a reading of data/signal uploaded to a computer-usable/computer readable storage medium.

The foregoing embodiments and other embodiments of the inventions of the present disclosure as well as various structures and advantages of the inventions of the present disclosure will become further apparent from the following detailed description of various embodiments of the inventions of the present disclosure read in conjunction with the accompanying drawings. The detailed description and drawings are merely illustrative of the inventions of the present disclosure rather than limiting, the scope of the inventions of the present disclosure being defined by the appended claims and equivalents thereof.

DETAILED DESCRIPTION OF THE PREFERRED EMBODIMENTS

To facilitate an understanding of various aspects of the present disclosure, the following description of FIGS. 1-10 teaches embodiments of a X-ray ring marker of the present disclosure. From this description, those having ordinary skill in the art will appreciate how to apply the various aspects of the present disclosure for making and using additional embodiments of X-ray ring markers of the present disclosure.

Figure 1:
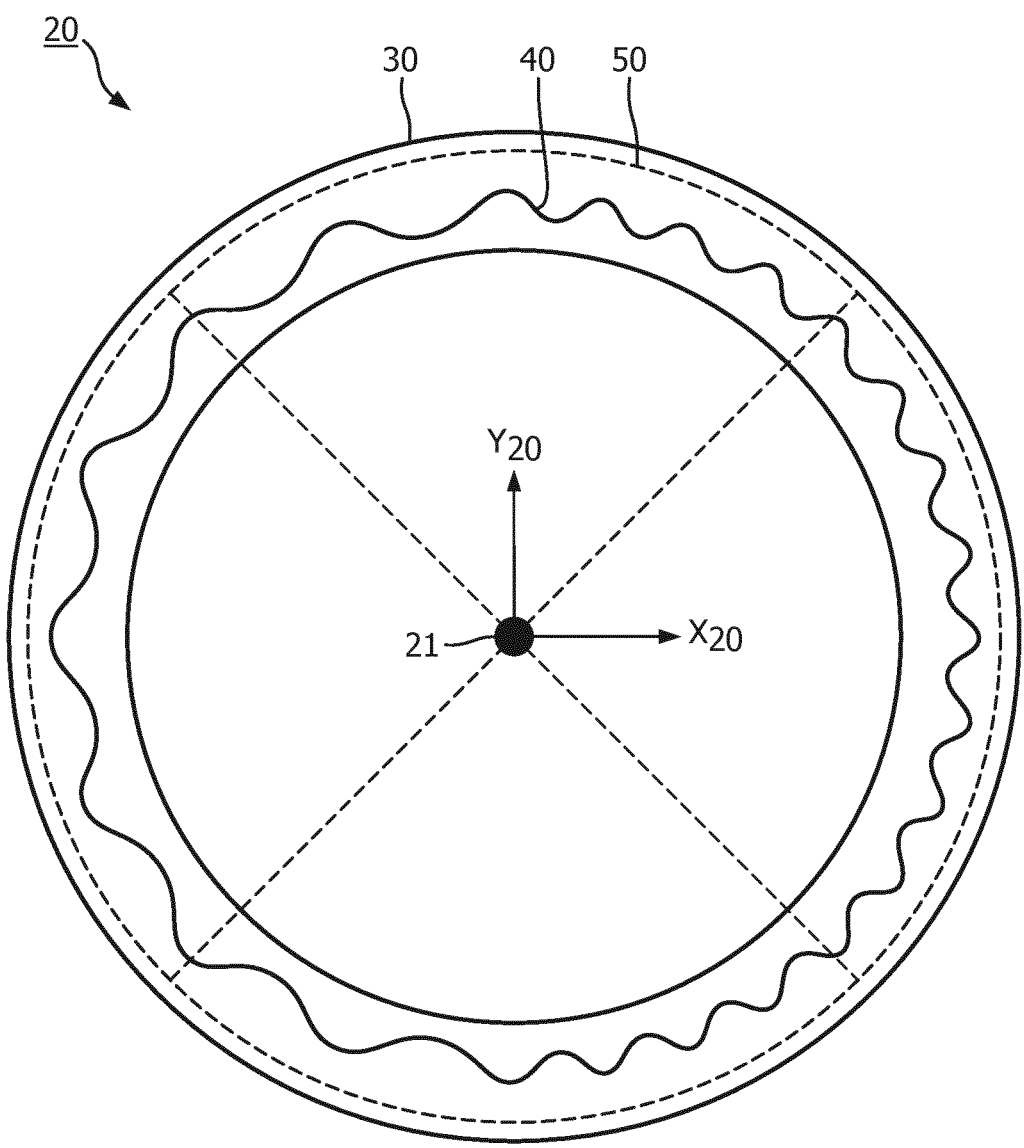
FIG. 1 illustrates an exemplary embodiment of a X-ray ring marker in accordance with various aspects of the present disclosure.

Referring to FIG. 1, a X-ray ring marker 20 of the present disclosure employs a coaxial construction of a chirp ring 40 and a centric ring 50 onto an annular base 30.

In practice, annular base 30 may have any annular shape suitable for a registration of C-arm to X-ray ring marker 30 including, but not limited to a circular shape and an elliptical shape.

Also in practice, annular base 30 may be constructed from material that is partially or entirely X-ray imageable.

Chirp ring 40 is a X-ray imageable annular structure embodying a chirp signal symbolically shown as a varying frequency waveform encircling annular base 30.

In one embodiment of chirp ring 40, the chirp signal is embodied as a varying spatial annular arrangement of protrusions formed in annular base 30.

In a second embodiment of chirp ring 40, the chirp signal is embodied as a varying spatial annular arrangement of indentations formed in annular base 30.

In a third embodiment of chirp ring 40, the chirp signal is embodied as a varying spatial annular arrangement of X-ray imageable objects disposed permanently or transiently onto/into annular base 30 (e.g., cooper balls, brass balls, etc.).

In practice, the chirp signal may have any amplitude, starting frequency and frequency shift suitable for an encoding of a twist of X-ray ring marker 20 around a Z-axis (not shown) of a C-Arm coordinate system as will be further described in the present disclosure.

Still referring to FIG. 1, centric ring 50 is a X-ray imageable annular spatial structure embodying center intersection points as symbolically shown as a dashed ring encircling annular base 30. The center intersection points define a center point 21 of X-ray ring marker 20 as symbolically shown by the dashed lines extending from centric ring 50 to center point 21.

In one embodiment of centric ring 50, the center intersection points are embodied as a symmetrical annular spatial arrangement of protrusions formed in annular base 30.

In a second embodiment of centric ring 50, the center intersection points are embodied as a symmetrical annular spatial arrangement of indentations formed in annular base 30.

In a third embodiment of a centric ring 50, the center intersection points are embodied as a symmetrical annular spatial arrangement of X-ray imageable objects disposed permanently or transiently disposed onto/into annular base 30 (e.g., cooper balls, brass balls, etc.).

In practice, centers of the chirp ring 40 and centric ring 50 are concentrically or eccentrically co-axially aligned along the Z-axis (not shown) of a coordinate system $X_{20}$-$Y_{20}$-$Z_{20}$ of X-ray ring marker 20 with center point 21 serving as on origin of coordinate system $X_{20}$-$Y_{20}$-$Z_{20}$.

Figure 2:
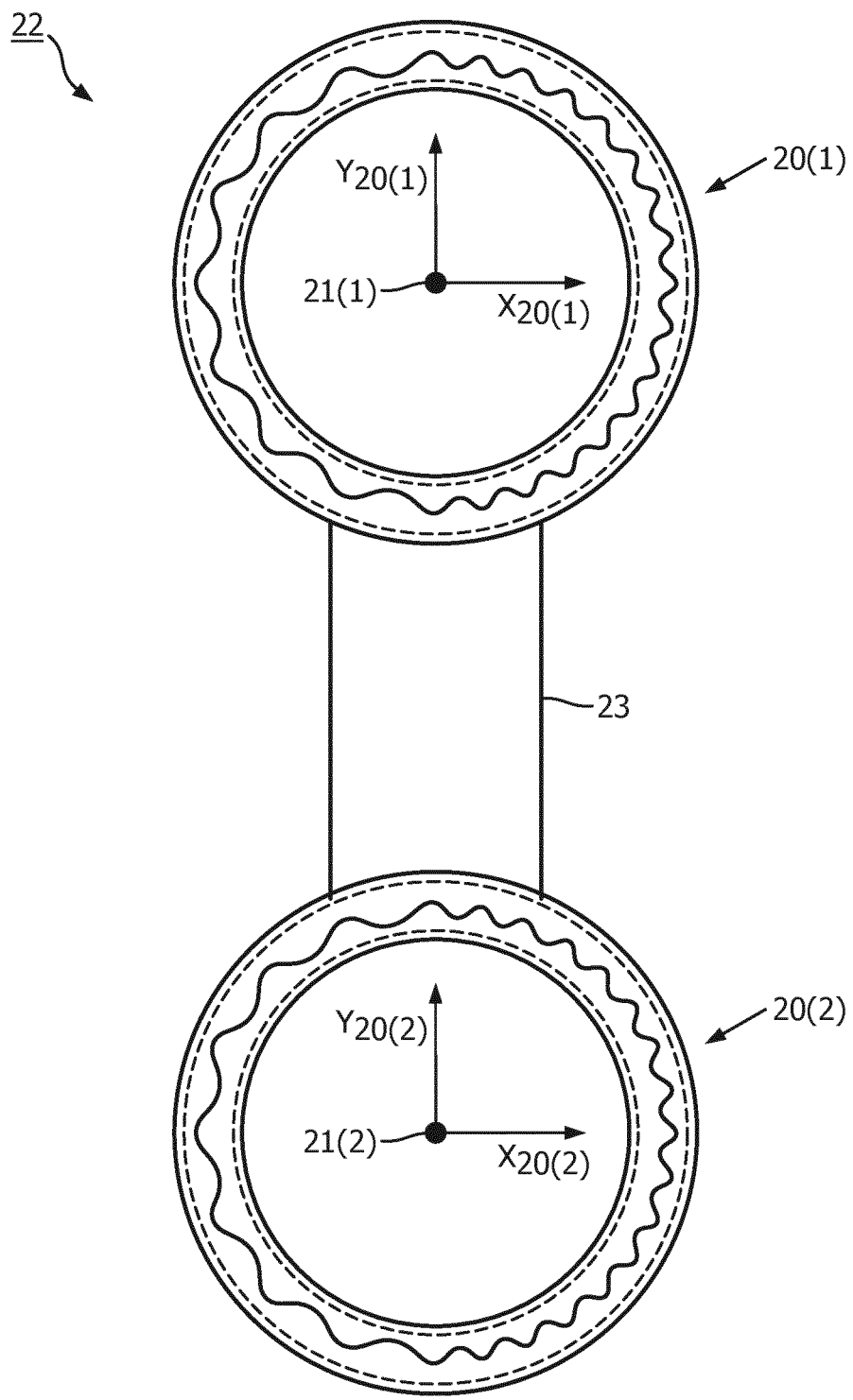
FIG. 2 illustrates an exemplary embodiment of a dual X-ray ring marker in accordance with various aspects of the present disclosure.

FIG. 2 illustrates a dual X-ray ring marker 22 of the present disclosure employing a pair of X-ray ring markers 20 of FIG. 1 of the present disclosure connected via a bridge 23. In practice, bridge 23 may be any shape suitable for a C-Arm→X-ray ring maker 20 registration involving a movement of C-arm from a baseline imaging pose to a target imaging pose as will be further described in the present disclosure, such as, for example, a prismatic shape of bridge 23 for establishing a co-planar alignment of the pair of X-ray ring markers 20 as shown in FIG. 2.

Figure 3A:
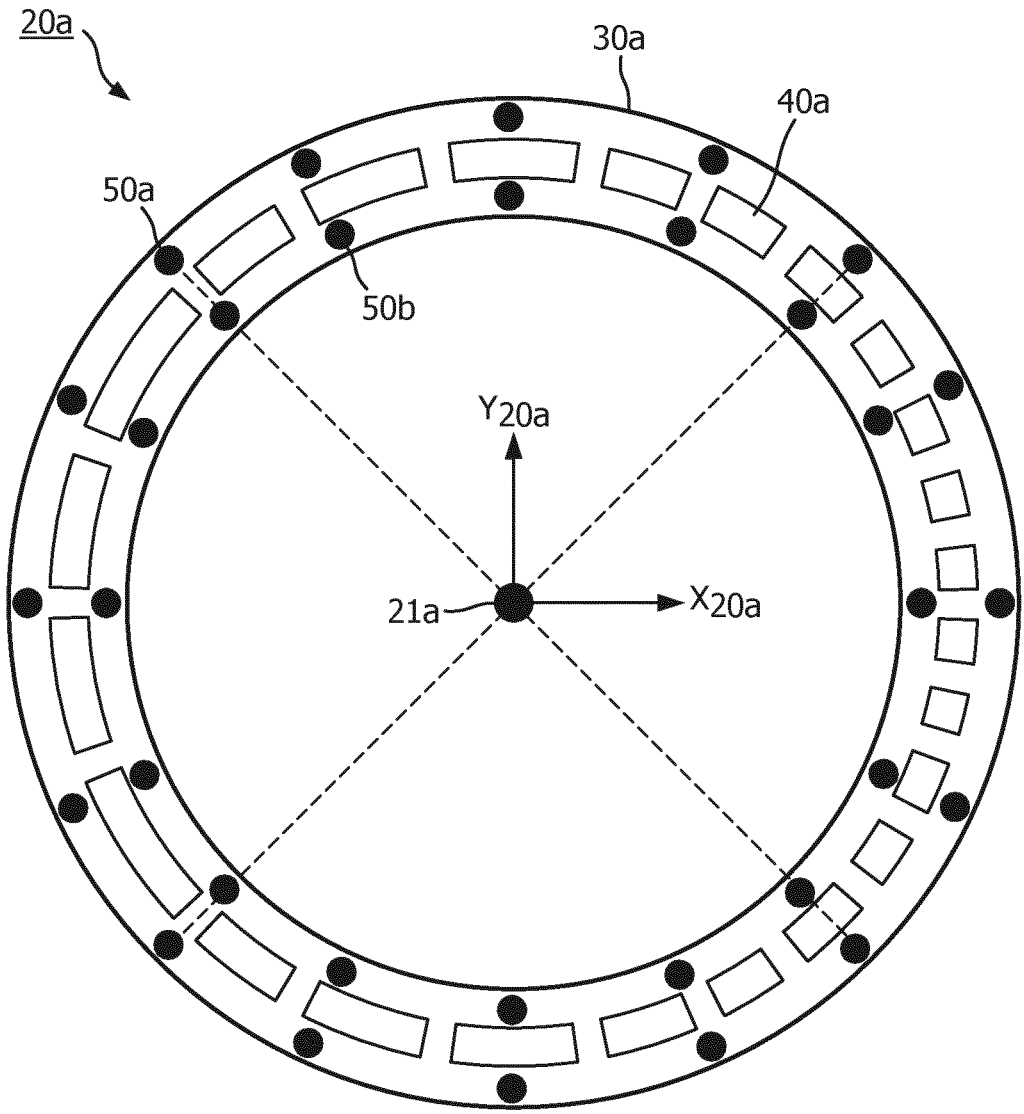
FIGS. 3A and 3B illustrate a first exemplary embodiment of the X-ray ring marker of FIG. 1 in accordance with various aspects of the present disclosure.
Figure 3B:
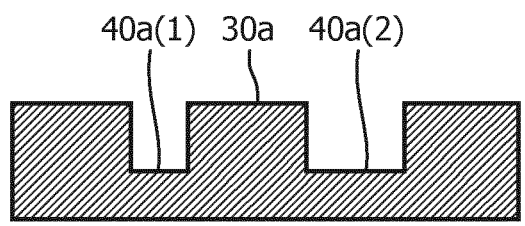

FIG. 3A illustrates an embodiment 20a of X-ray ring marker 20 of FIG. 1 of the present disclosure. X-ray ring marker 20a employs an annular base 30a having a chirp ring embodied as an annular spatial arrangement of indentations 40a formed in annular base 30a as exemplary shown in FIG. 3B. The dimensions of the indentations 40a vary along a 360° traversal of annular base 30a to define a chirp signal.

Still referring to FIG. 3A, centric ring 50 as shown in FIG. 1 of the present disclosure is embodied by an outer circle of uniformly spaced objects 50a (e.g., cooper balls, brass balls, etc.) affixed adjacent an outer perimeter of annular base 30a, and an inner circle of uniformly spaced objects 50b (e.g., cooper balls, brass balls, etc.) affixed adjacent an inner perimeter of annular base 30a. Each object 50a of the outer circle is paired with a corresponding object 50b of the inner circle to define an intersection line of a center point 21a of X-ray ring marker 20a serving as an origin of a coordinate system $X_{20a}$-$Y_{20a}$-$Z_{20a}$ of X-ray ring marker 20a (Z-axis not shown).

Figure 4:
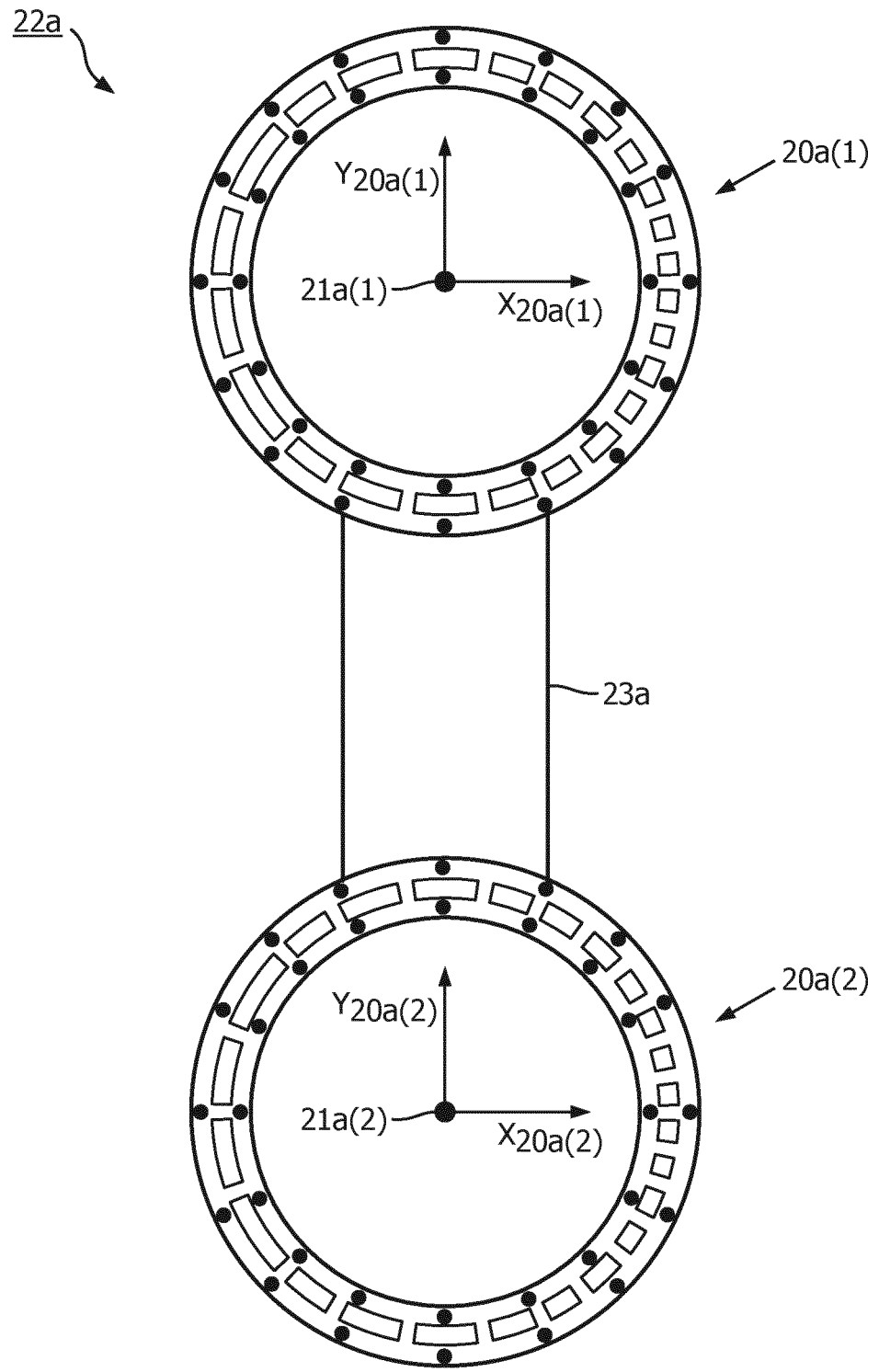
FIG. 4 illustrates a first exemplary embodiment of the dual X-ray ring marker of FIG. 2 in accordance with various aspects of the present disclosure.

FIG. 4 illustrates a dual X-ray ring marker 22a of the present disclosure employing a pair of X-ray ring markers 20a of FIG. 3A of the present disclosure connected via a bridge 23a. In practice, bridge 23a may be any shape suitable for a C-Arm→X-ray ring maker 20a registration involving a movement of C-arm from a baseline imaging pose to a target imaging pose as will be further described in the present disclosure, such as, for example, a prismatic shape of bridge 23a for establishing a co-planar alignment of the pair of X-ray ring markers 20a as shown in FIG. 4.

Figure 5A:
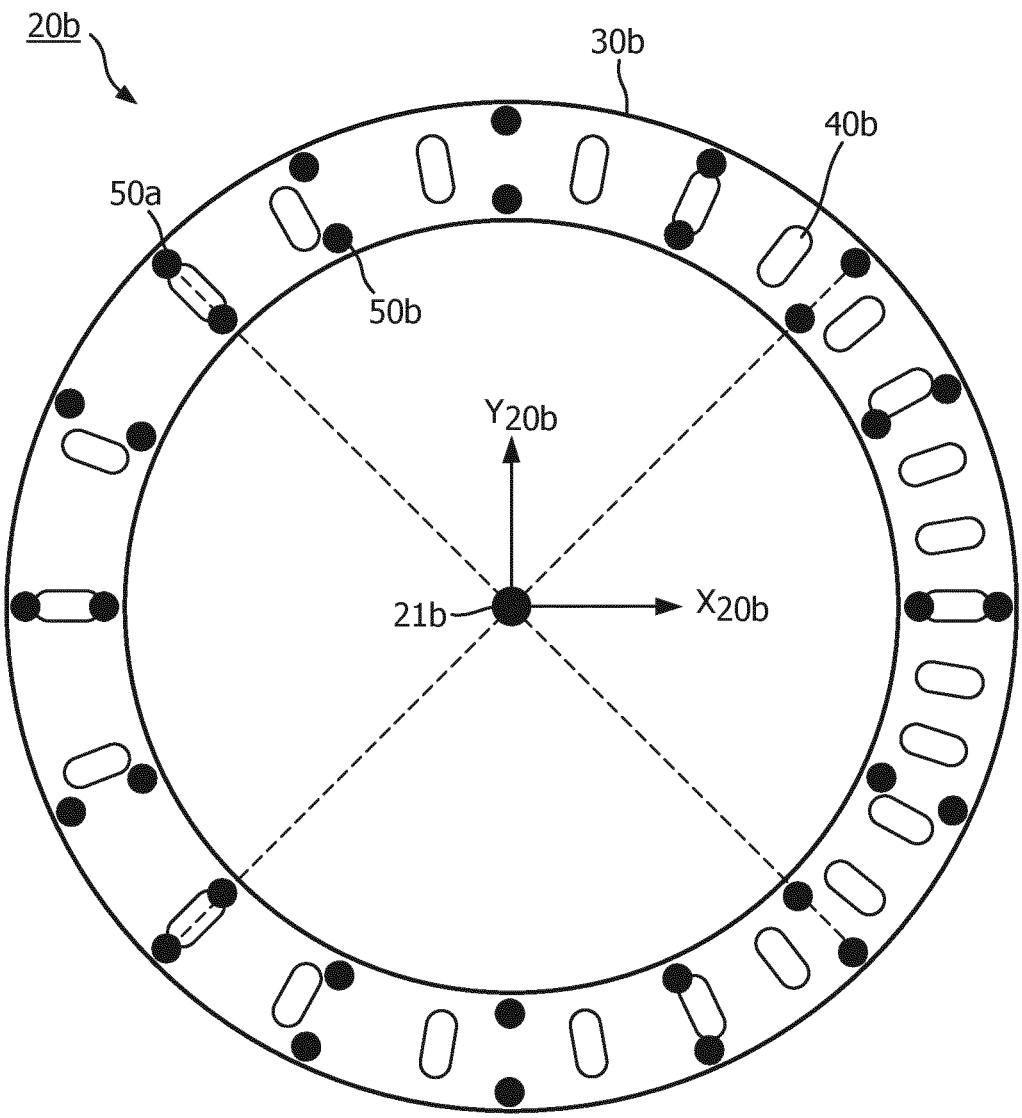
FIGS. 5A and 5B illustrate a second exemplary embodiment of the X-ray ring marker of FIG. 1 in accordance with various aspects of the present disclosure.
Figure 5B:
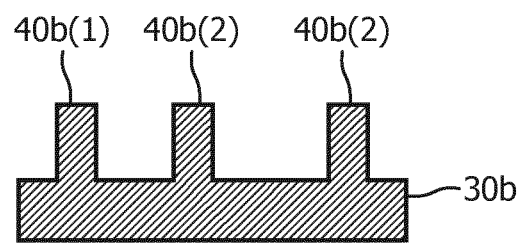

FIG. 5A illustrates an embodiment 20b of X-ray ring marker 20 of FIG. 1 of the present disclosure. X-ray ring marker 20b employs an annular base 30b having a chirp ring embodied as an annular spatial arrangement of protrusions 40b formed in annular base 30b as exemplary shown in FIG. 5B. The dimensions of protrusions 40b vary along a 360° traversal of annular base 30b to define a chirp signal.

Still referring to FIG. 5A, centric ring 50 as shown in FIG. 1 of the present disclosure is again embodied by an outer circle of uniformly spaced objects 50a (e.g., cooper balls, brass balls, etc.) affixed adjacent an outer perimeter of annular base 30b, and an inner circle of uniformly spaced objects 50b (e.g., cooper balls, brass balls, etc.) affixed adjacent an inner perimeter of annular base 30b. Each object 50a of the outer circle is paired with a corresponding object 50b of the inner circle to define an intersection line of a center point 21b of X-ray ring marker 20b serving as an origin of a coordinate system $X_{20b}$-$Y_{20b}$-$Z_{20b}$ of X-ray ring marker 20b (Z-axis not shown).

Figure 6:
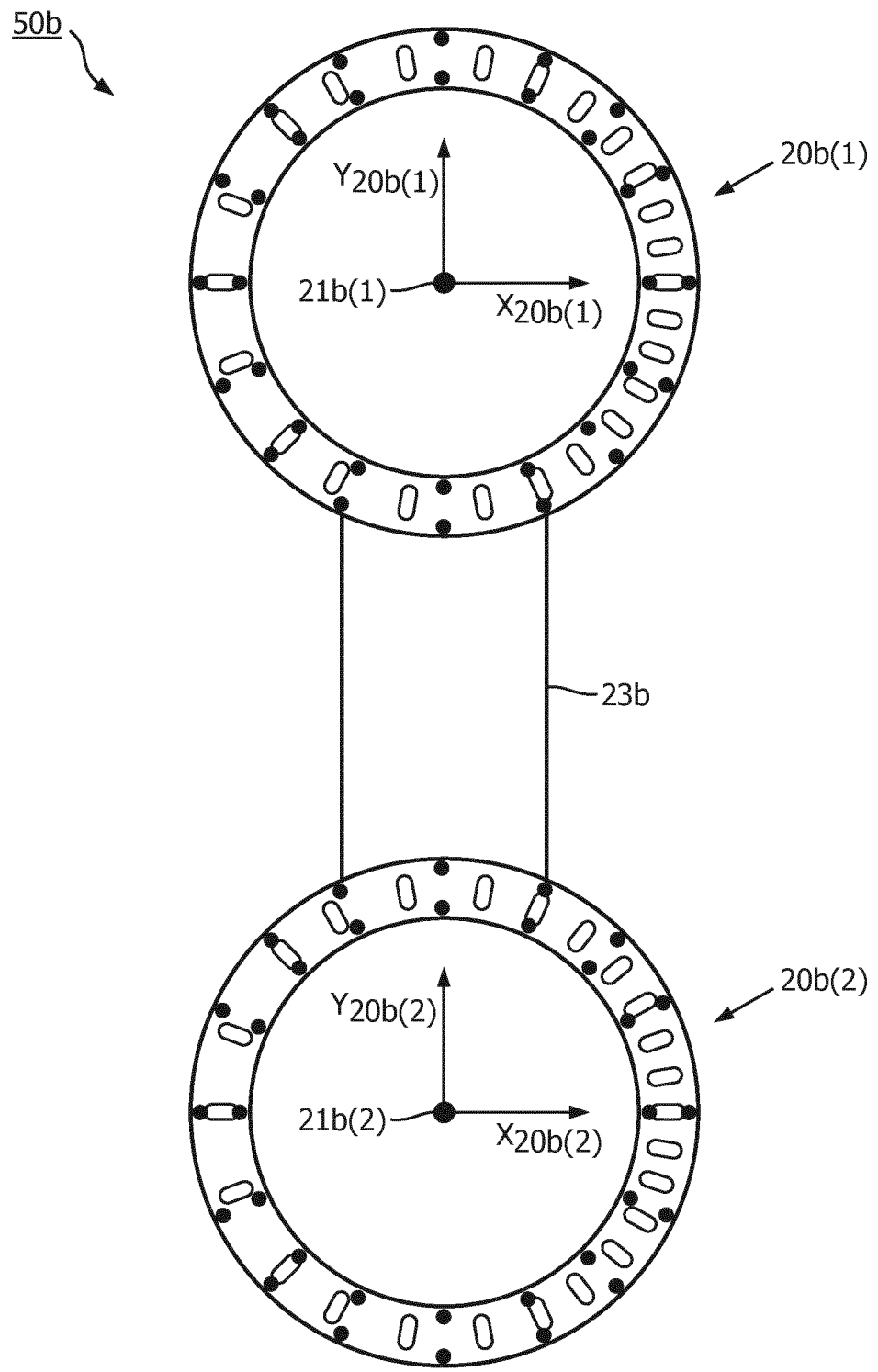
FIG. 6 illustrates a second exemplary embodiment of the dual X-ray ring marker of FIG. 2 in accordance with various aspects of the present disclosure.

FIG. 6 illustrates a dual X-ray ring marker 22b of the present disclosure employing a pair of X-ray ring markers 20b of FIG. 5A of the present disclosure connected via a bridge 23b. In practice, bridge 23b may be any shape suitable for a C-Arm→X-ray ring maker 20 registration involving a movement of C-arm from a baseline imaging pose to a target imaging pose as will be further described in the present disclosure, such as, for example, a prismatic shape of bridge 23b for establishing a co-planar alignment of the pair of X-ray ring markers 20b as shown in FIG. 6.

Figure 7:
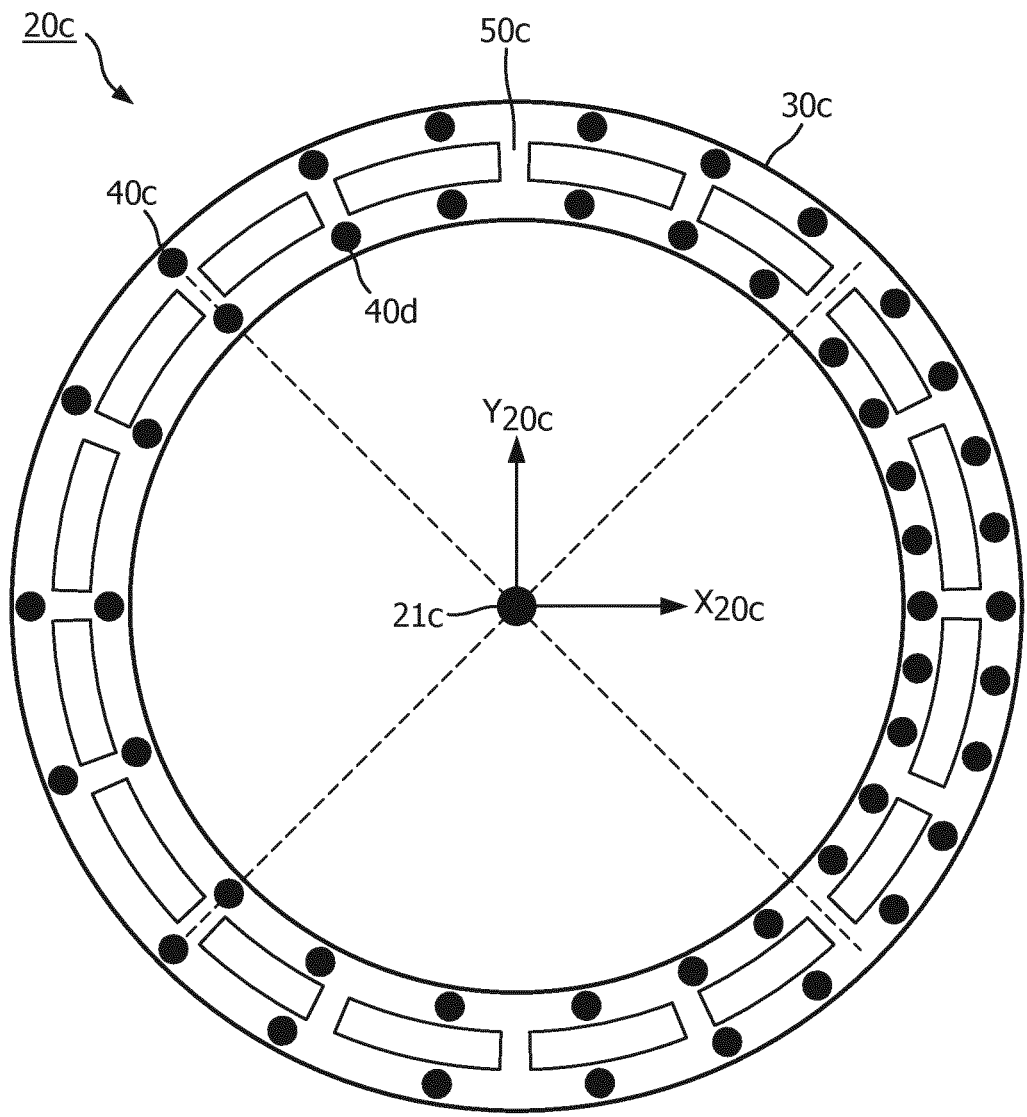
FIG. 7 illustrates a third exemplary embodiment of the X-ray ring marker of FIG. 1 in accordance with various aspects of the present disclosure.

FIG. 7 illustrates an embodiment 20c of X-ray ring marker 20 of FIG. 1 of the present disclosure. X-ray ring marker 20c employs an annular base 30c having a chirp ring embodied by an outer circle of varyingly spaced objects 40c (e.g., cooper balls, brass balls, etc.) affixed adjacent an outer perimeter of annular base 30c, and an inner circle of varyingly spaced objects 40d (e.g., cooper balls, brass balls, etc.) affixed adjacent an inner perimeter of annular base 30c. The spacing of the objects 40c and 40d vary along a 360° traversal of annular base 30c to define a chirp signal.

Still referring to FIG. 7, X-ray ring marker 20c further employs a centric ring embodied as uniformly spaced protrusions 50c formed into annular base 30c. Each protrusion 50c is paired with a corresponding 180° protrusion 50c to define intersection lines of a center point 21c of X-ray ring marker 20c serving as an origin of a coordinate system $X_{20c}$-$Y_{20c}$-$Z_{20c}$ of X-ray ring marker 20c (Z-axis not shown).

In an alternative embodiment, centric ring may be embodied as uniformly spaced indentations formed into annular base 30c. Each indentations would be paired with a corresponding 180° indentation to define intersection lines of center point 21c of X-ray ring marker 20c.

Figure 8:
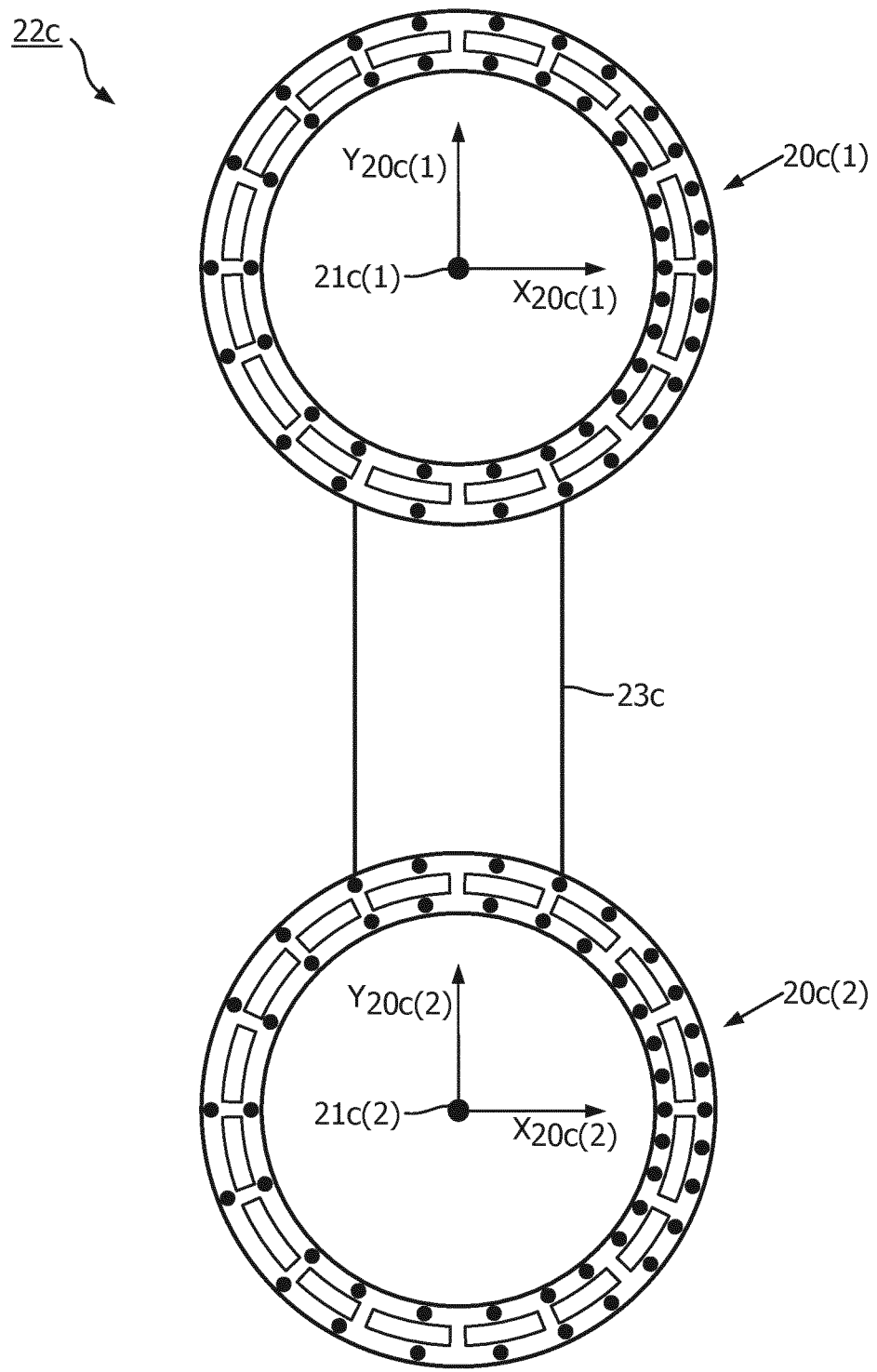
FIG. 8 illustrates a third exemplary embodiment of the dual X-ray ring marker of FIG. 2 in accordance with various aspects of the present disclosure.

FIG. 8 illustrates a dual X-ray ring marker 22c of the present disclosure employing a pair of X-ray ring markers 20c of FIG. 7 of the present disclosure connected via a bridge 23c. In practice, bridge 23c may be any shape suitable for a C-Arm→X-ray ring maker 20 registration involving a movement of C-arm from a baseline imaging pose to a target imaging pose as will be further described in the present disclosure, such as, for example, a prismatic shape of bridge 23c for establishing a co-planar alignment of the pair of X-ray ring markers 20c as shown in FIG. 8.

Figure 9:
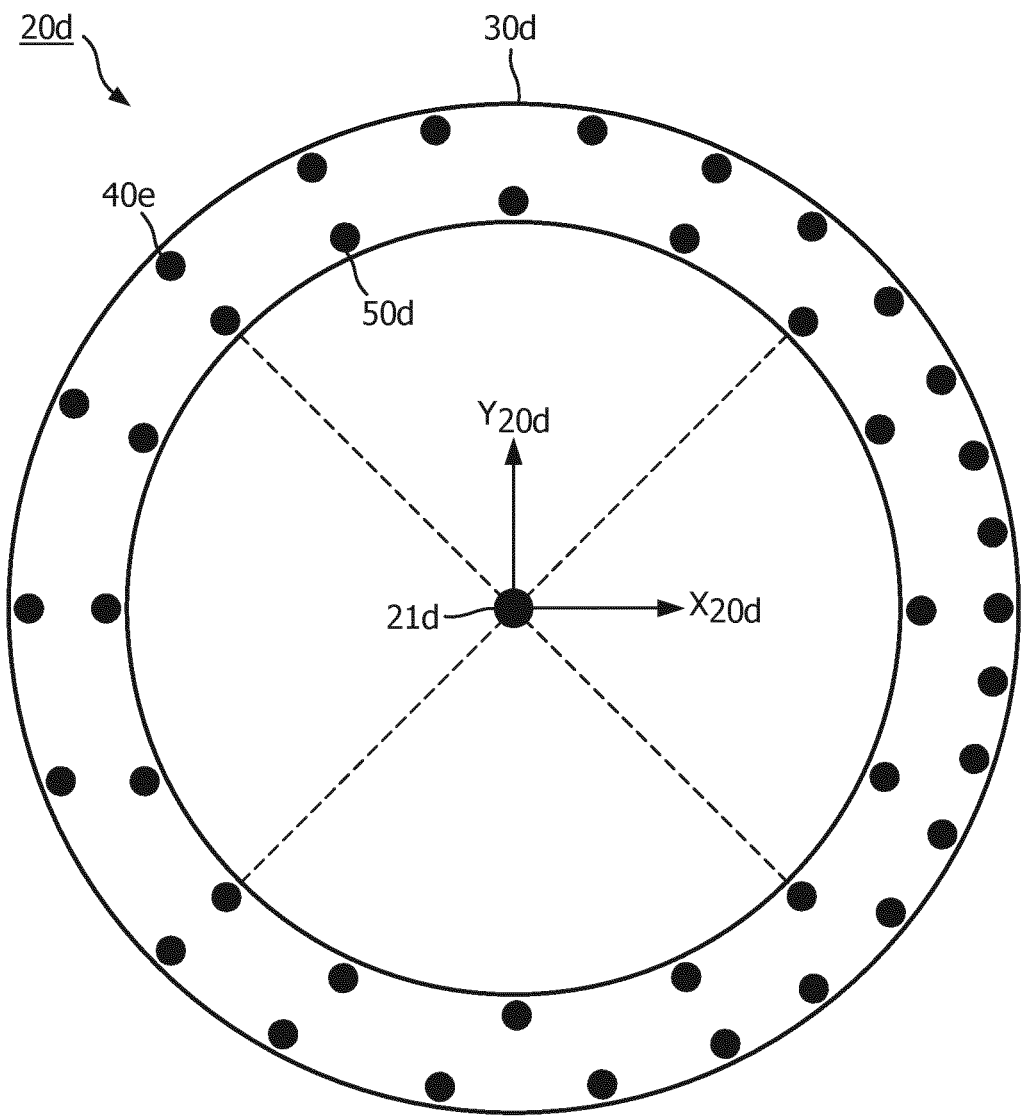
FIG. 9 illustrates a fourth exemplary embodiment of the X-ray ring marker of FIG. 1 in accordance with various aspects of the present disclosure.

FIG. 9 illustrates an embodiment 20d of X-ray ring marker 20 of FIG. 1 of the present disclosure. X-ray ring marker 20d employs an annular base 30d having a chirp ring embodied by an outer circle of varyingly spaced objects 40e (e.g., cooper balls, brass balls, etc.) affixed adjacent an outer perimeter of annular base 30d. The spacing of the objects 40e vary along a 360° traversal of annular base 30d to define a chirp signal.

Still referring to FIG. 9, X-ray ring marker 20d further employs a centric ring embodied an inner circle of varyingly spaced objects 50d (e.g., cooper balls, brass balls, etc.) affixed adjacent an inner perimeter of annular base 30d. Each object 50d is paired with a corresponding 180° object 50d to define intersection lines of a center point 21d of X-ray ring marker 20d serving as an origin of a coordinate system $X_{20d}$-$Y_{20d}$-$Z_{20d}$ of X-ray ring marker 20d (Z-axis not shown).

Figure 10:
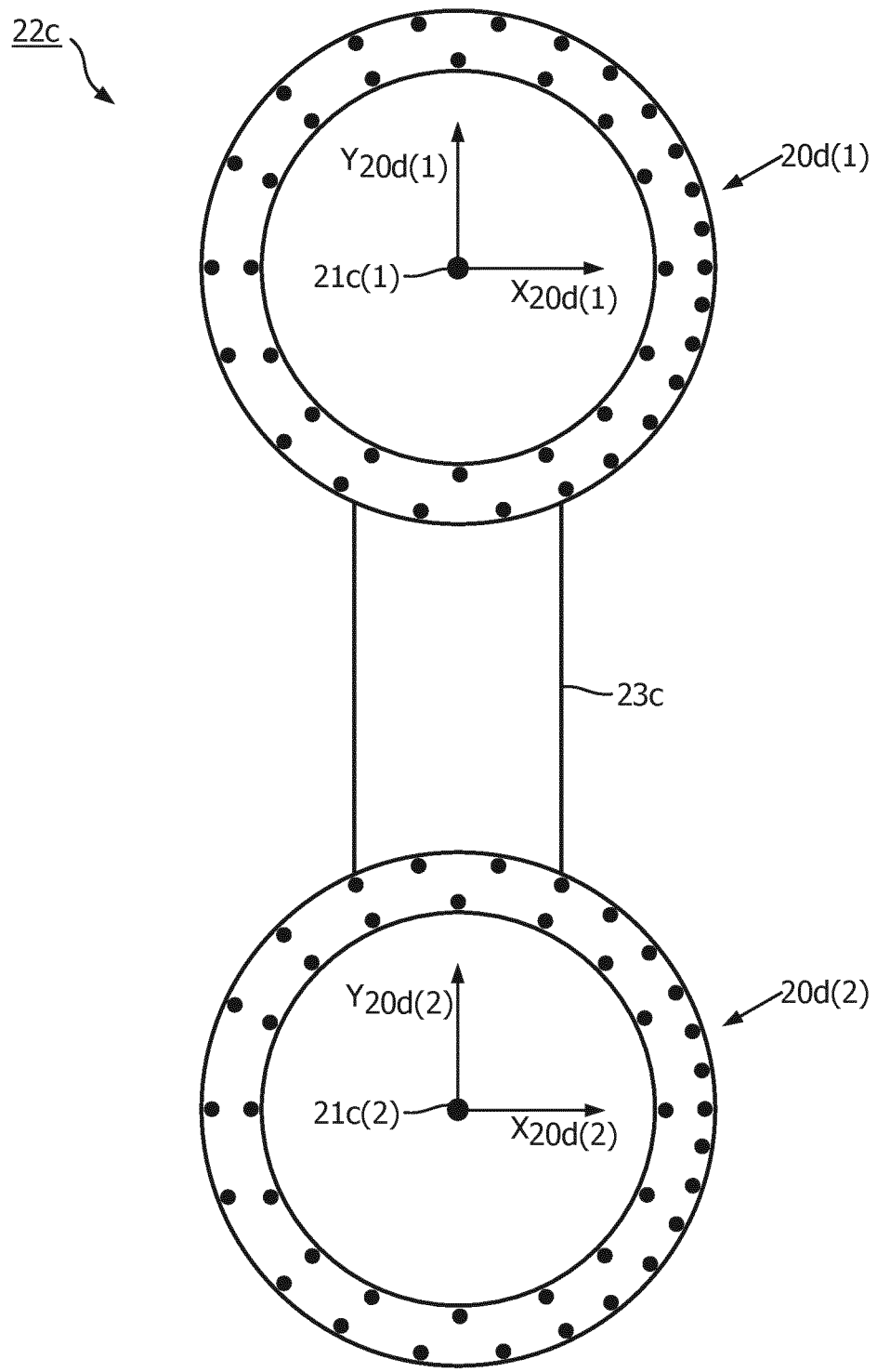
FIG. 10 illustrates a fourth exemplary embodiment of the dual X-ray ring marker of FIG. 2 in accordance with various aspects of the present disclosure.

FIG. 10 illustrates a dual X-ray ring marker 22d of the present disclosure employing a pair of X-ray ring markers 20d of FIG. 7 of the present disclosure connected via a bridge 23d. In practice, bridge 23d may be any shape suitable for a C-Arm→X-ray ring maker 20 registration involving a movement of C-arm from a baseline imaging pose to a target imaging pose as will be further described in the present disclosure, such as, for example, a prismatic shape of bridge 23d for establishing a co-planar alignment of the pair of X-ray ring markers 20d as shown in FIG. 10.

To further facilitate an understanding of various aspects of the present disclosure, the following description of FIGS. 11-18 teaches embodiments of a C-Arm Arm→X-ray ring maker registration of the present disclosure. From this description, those having ordinary skill in the art will appreciate how to apply various aspects of the present disclosure for making and using additional embodiments of C-Arm→X-ray ring maker registration of the present disclosure.

In practice, a C-Arm→X-ray ring maker registration of the present disclosure may be implemented in a baseline phase and a target phase for generating registration parameters to facilitate a wide range of C-Arm intervention technologies including, but not limited to, robot three-dimensional measurements, anatomical/implant tracking, image stitching, pre-operative image overlay and first-time-right C-Arm positioning.

Figure 11A:
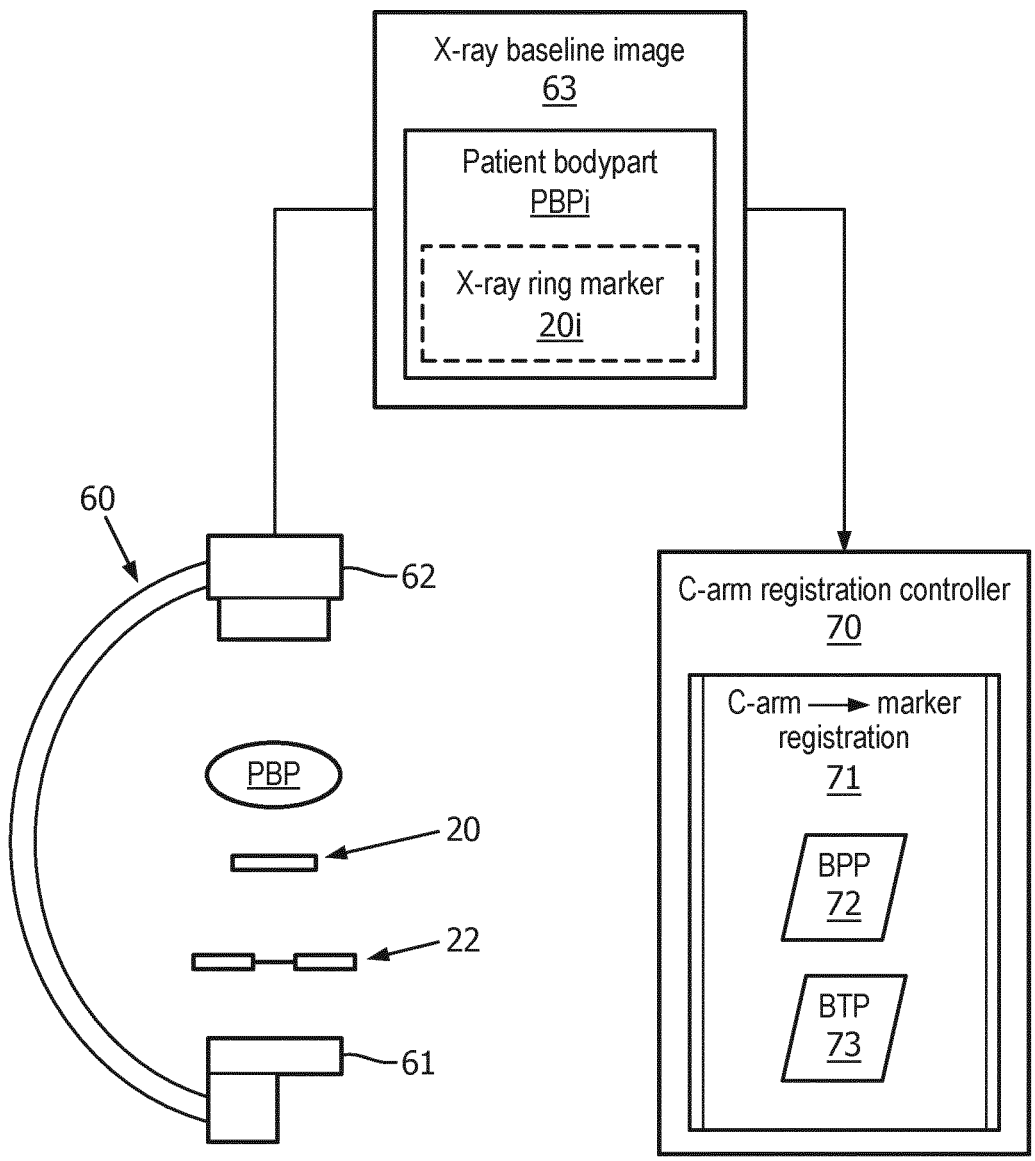
FIG. 11A illustrates an exemplary embodiment of a baseline phase of a C-Arm→X-ray ring marker registration in accordance with various aspects of the present disclosure.

Referring to FIG. 11A, generally in the baseline phase, an embodiment of X-ray ring marker 20 as shown in FIG. 1 of the present disclosure or an embodiment of dual X-ray ring marker 22 shown in FIG. 2 of the present disclosure has a fixed position within an intervention space (e.g., an attachment to an operating table, a rail, a drape, or an intervention robot) and a body part of interest of a patient PBP is positioned above and adjacent X-ray ring marker 20 or dual X-ray ring marker 22.

A X-ray source 61 and a X-ray detector 62 of a C-Arm 60 are positioned in a baseline imaging pose to generate a baseline X-ray image 63 illustrating an image of X-ray ring marker 20i below an image of patient body part PBPi.

A C-Arm registration controller 70 acquires data of baseline X-ray image 63 and executes a C-Arm→X-ray ring marker registration 71 of the present disclosure to derive baseline position parameters 72 and a baseline twist parameter 73 as a first subset of the registration parameters as will be further described in the present disclosure.

Figure 11B:
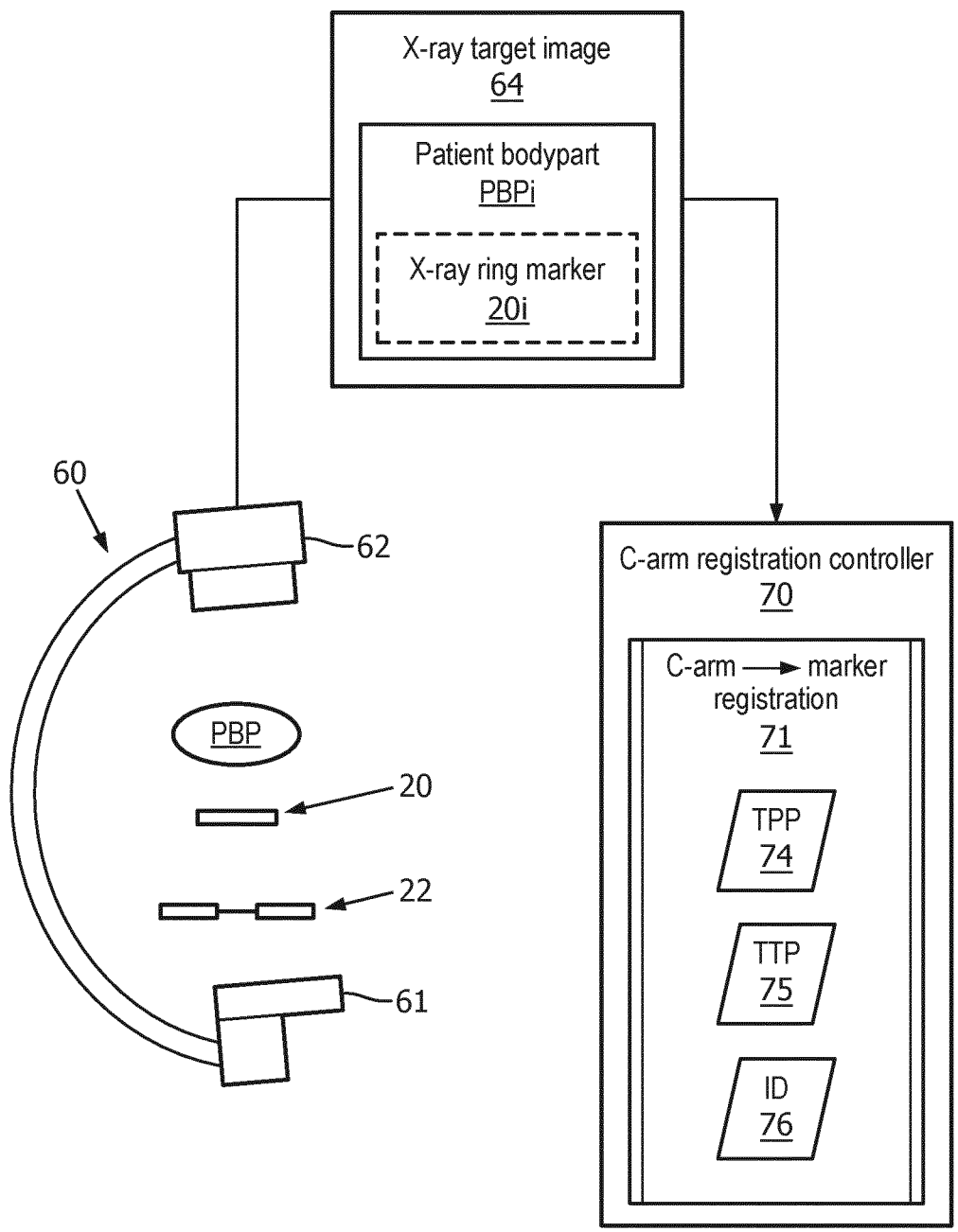
FIG. 11B illustrates an exemplary embodiment of a target phase of a C-Arm→X-ray ring marker registration in accordance with various aspects of the present disclosure.

Referring to FIG. 11B, generally in the target phase, X-ray source 61 and X-ray detector 62 of C-Arm 60 are moved from the baseline imaging pose to a target imaging pose, such as, for example, a rotation of C-arm 60 from the baseline imaging pose of FIG. 11A of the present disclosure to a target imaging pose of FIG. 11B. At the target imaging pose, X-ray source 61 and X-ray detector 62 of C-Arm 60 are positioned to generate a target X-ray image 64 illustrating an image of X-ray ring marker 20i below an image of patient body part PBPi.

C-Arm registration controller 70 acquires target X-ray image 64 and executes C-Arm→X-ray ring marker registration 71 of the present disclosure to derive target position parameters 74 and a target twist parameter 75 as a second final subset of the registration parameters as will be further described in the present disclosure.

C-Arm registration controller 70 may further execute C-Arm→X-ray ring marker registration 71 to implement of one or more intervention steps to generate intervention data 76 based on the registration parameters.

In practice, any imaging pose of a C-arm may serve as a baseline imaging pose for one C-Arm→X-ray ring marker registration during an intervention/diagnostic/imaging procedure, and may serve as a target imaging pose for another C-Arm→X-ray ring marker registration during the same or different intervention/diagnostic/imaging procedure.

Figure 12:
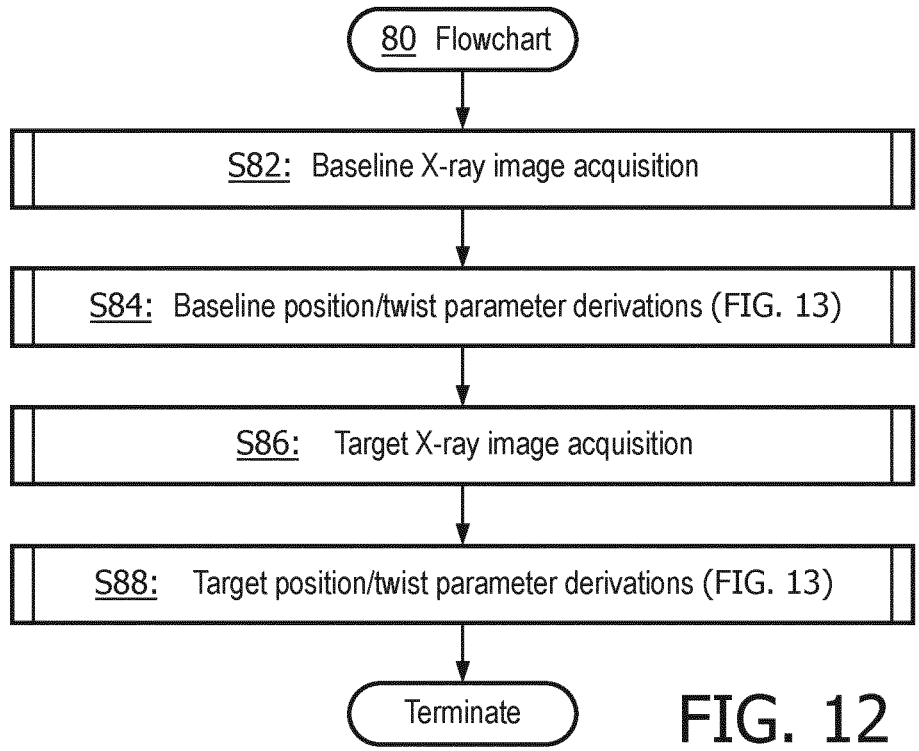
FIG. 12 illustrates a flowchart representative of an exemplary embodiment of a C-Arm X-ray ring marker registration method in accordance with various aspects of the present disclosure.

FIG. 12 illustrates a flowchart 80 representative of an embodiment of C-Arm→X-ray ring marker registration 71. To facilitate an understanding of flowchart 80, FIG. 12 will be described in reference to FIGS. 11A, 11B, 14A and 14B. From this description, those having ordinary skill in the art will appreciate how to apply flowchart 80 to numerous and various additional embodiments of C-Arm→X-ray ring marker registration 71.

Figure 14A:
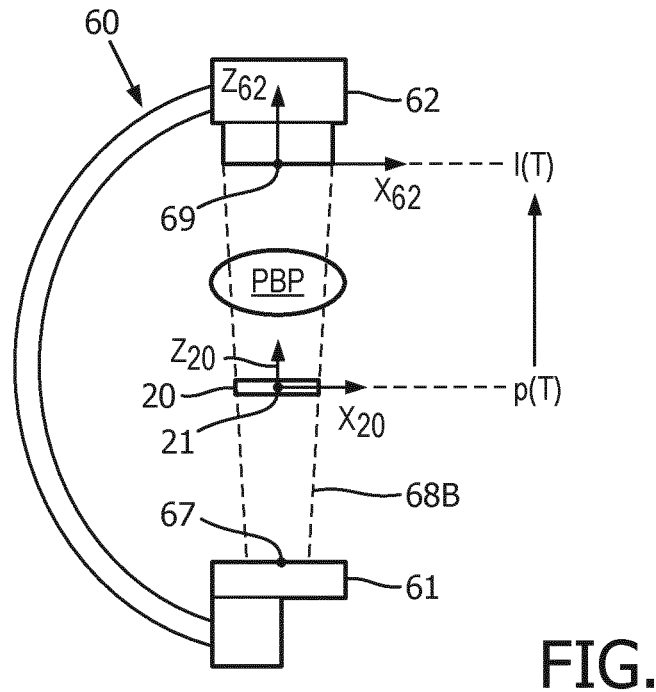
FIG. 14A illustrates an exemplary baseline imaging pose of a C-Arm in accordance with the various aspects of the present disclosure.

Referring to FIGS. 11A and 12, a stage S82 of flowchart 80 encompasses an acquisition by controller 70 of baseline X-ray image 63 from C-arm 60 as known in the art of the present disclosure. More particularly during the baseline phase, as shown in FIG. 14A, the C-Arm→X-ray ring marker registration 71 involves registering a position and a twist of X-ray ring marker 20 of the present disclosure within a X-ray projection 68B originating from a focal spot 67 of X-ray source 61 to X-ray detector 62.

In practice, a $X_{62}$-$Y_{62}$-$Z_{62}$ coordinate system of C-Arm 60 may be defined on X-ray detector 62 whereby the X-axis and the Y-axis of the coordinate system of C-Arm 60 may be aligned with a coordinate system of the baseline X-ray image, such as, for example a $X_{65a}$-$Y_{65a}$ coordinate system of baseline X-ray image 63 shown in FIG. 11A. An origin 69 of $X_{62}$-$Y_{62}$-$Z_{62}$ coordinate system of C-Arm 60 may be delineated whereby X-ray source 62 is on a positive range of a $Z_{62}$ axis of $X_{62}$-$Y_{62}$-$Z_{62}$ coordinate system of C-Arm 60 whereby focal spot 67 of X-ray source 61 has a (0, 0, +$Z_{62}$) coordinate within $X_{62}$-$Y_{62}$-$Z_{62}$ coordinate system of C-Arm 60.

Referring back to FIGS. 11A and 12, a stage S84 of flowchart 80 encompasses controller 70 deriving baseline position parameters $t_x^B$, $t_y^B$, $t_z^B$, $\theta_{z1}^B$ and $\theta_x^B$ of X-ray ring marker 20 as a function of an illustration of the centric ring within the baseline X-ray image 63. The baseline position parameters $t_x^B$, $t_y^B$, $t_z^B$, $\theta_{z1}^B$ and $\theta_x^B$ are definitive of a position of X-ray ring marker 20 within the baseline X-ray projection 68B.

Stage S84 of flowchart 80 further encompasses controller 70 deriving a baseline twist parameter $\theta_{z2}^B$ of X-ray ring marker 20 as a function of the baseline position parameters $t_x^B$, $t_y^B$, $t_z^B$, $\theta_{z1}^B$ and $\theta_x^B$ of an illustration of the chirp ring within the baseline X-ray image 63. The baseline twist parameter $\theta_{z2}^B$ is definitive of a twist of the X-ray ring marker 20 within the baseline X-ray projection 68B.

Figure 13:
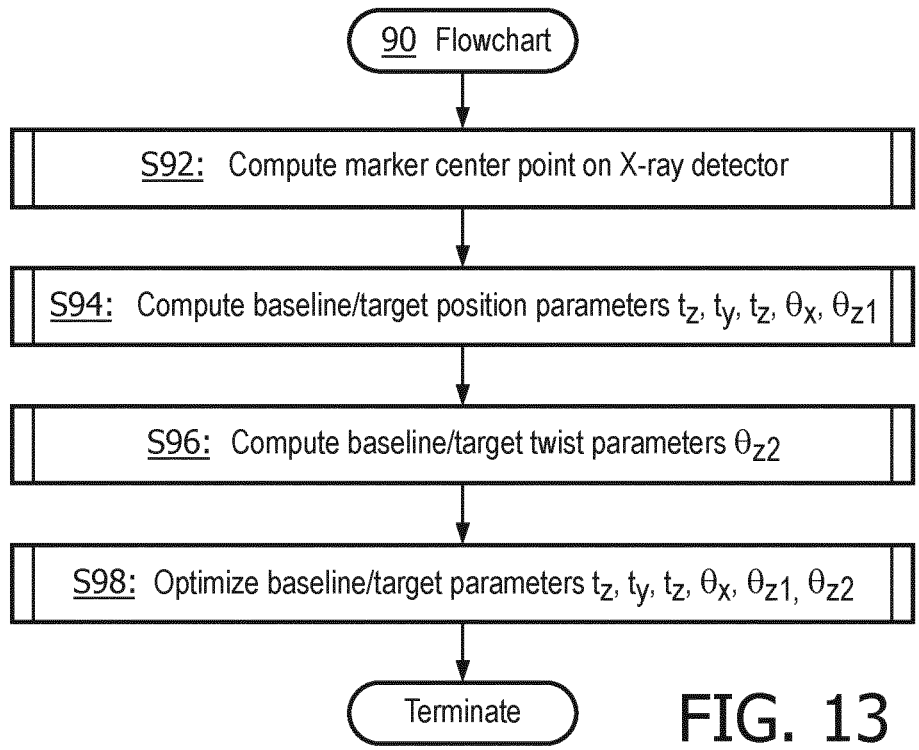
FIG. 13 illustrates a flowchart representative of an exemplary embodiment of a registration parameter computation method in accordance with various aspects of the present disclosure.

In one embodiment of stage S84, controller 70 executes a registration parameter computation method of the present disclosure represented by a flowchart 90 of FIG. 13.

Referring to FIGS. 13 and 14A, a stage S92 of flowchart 90 encompasses a computation of a center point 21 of X-ray ring marker 20 on X-ray detector 62.

In one embodiment of stage S92 with spherical objects (e.g., cooper balls or brass balls. etc.), an identification of the spherical objects as illustrated within baseline X-ray image 63 starts with an adaptive thresholding technique as known in the art of the present disclosure to identify imaging blobs within the baseline X-ray image 63 followed by a series of morphological operations to eliminate blobs having a smaller size relative to the size of the spherical objects.

From the remaining image blobs within the baseline X-ray image, image blobs having an aspect ratio close to round and areas between certain thresholds are selected as candidate spherical objects radial pairs whereby blob pairs with a distance therebetween within a certain range are selected as radial pairs whereby an intersection of all lines defined by radial pairs are computed using a least square approach providing a residual. A robustness of identification of the spherical objects as illustrated within a baseline X-ray image 63 is improved by iteratively eliminating candidate spherical objects that lead to large residual values.

The result of stage S92 is a following listing of an M number of paired objects in the C-Arm coordinate system: $\{[(X_1^1, Y_1^1), (X_1^2, Y_1^2)] \ldots [(X_M^1, Y_M^1), (X_M^2, Y_M^2)]\}$, $M \geq 2$.

Still referring to FIGS. 13 and 14A, stage S92 further encompasses controller 70 delineating intersection lines between paired objects $\{[(X_1^1, Y_1^1), (X_1^2, Y_1^2)] \ldots [(X_M^1, Y_M^1), (X_M^2, Y_M^2)]\}$, $M \geq 2$, within the baseline X-ray image 63 to compute a projection $(X_C, Y_C)$ of a center of the X-ray ring marker 20 on the X-ray detector 62.

Referring back to FIGS. 13 and 14A, a stage S94 of flowchart 90 encompasses controller 70 utilizing the projection $(X_C, Y_C)$ of a center point 21 of the X-ray ring marker 20 on the X-ray detector 62 during stage S92 to compute baseline position parameters $t_x^B$, $t_y^B$, $t_z^B$, $\theta_{z1}^B$ and $\theta_x^B$.

In one embodiment of stage S94, based on the projection $(X_C, Y_C)$ of a center point 21 of the X-ray ring marker 20 on the X-ray detector 62, the projection ray defining the center point 21 of the X-ray ring marker 20 extend from source point (0, 0, $S_d^B$) to detector point $(X_C, Y_C, 0)$. This means that the center point 21 of the X-ray ring marker 20 may be parameterized by the following equation [1]:

$$\begin{pmatrix} t_x^B \\ t_y^B \\ t_z^B \end{pmatrix} = \begin{pmatrix} X_C^B \dfrac{S_d^B - t_z^B}{S_d^B} \\ Y_C^B \dfrac{S_d^B - t_z^B}{S_d^B} \\ t_z^B \end{pmatrix}; \quad [1]$$

$$t_z^B \in (0, S_d^B)$$

Assuming the listed object points $\{[(X_1^1, Y_1^1), (X_1^2, Y_1^2)] \ldots [(X_M^1, Y_M^1), (X_M^2, Y_M^2)]\}$ is such that the first point belongs to inner centering circle of a radius $R_I$ and the belongs to an the outer centering circle of a radius $R_O$, a cost function may be defined with parameters $t_z^B$, $\theta_{z1}^B$ and $\theta_x^B$ as a measure of how well the object points fit X-ray ring marker 20 placed at a location $(t_x^B, t_y^B, t_z^B)^T$ and angulation $\theta_{z1}^B$ and $\theta_x^B$.

In one embodiment, the cost function is constructed as follows.

First, a cost CF is initialized at a value of zero (0).

Second, for each landmark pair $\{[(X_i^1, Y_i^1), (X_i^2, Y_i^2)]\}$:

a. a computation of an intersection between segment $\{[(X_i^1, Y_i^1, 0), (0, 0, S_d^B)]_1\}$ and marker XY plane assuming that the X-ray ring marker 20 is at a location $(t_x^B, t_y^B, t_z^B)^T$ and angulation $\theta_{z1}^B$ and $\theta_x^B$. This point is $(Xsol_1, Ysol_1, 0)$ in the marker coordinate system;

b. a closest point on the circle to $(Xsol_1, Ysol_1, 0)$ is $(Xr_1, Yr_1, 0) = (R_1 \cos(\phi_1), R_1 \sin(\phi_1), 0)$, where $\phi_1$–a tan $2(Ysol_1, Xsol_1)$;

c. the square distance between the two points is $dsq_1 = (Xsol_1 - xr_1)^2 + (Ysol_1 - yr_1)^2$ d. update cost function CF+=$dsq_1$;

e. a computation of an intersection between segment $\{[(X_i^2, Y_i^2, 0), (0, 0, S_d^B)]\}$ and marker XY plane assuming that the X-ray ring marker 20 is at a location $(t_x^B, t_y^B, t_z^B)^T$ and angulation $\theta_{z1}^B$ and $\theta_x^B$. This point is $(xsol_2, ysol_2, 0)$ in the marker coordinate system;

f. a closest point on the circle to $(Xsol_2, Ysol_2, 0)$ is $(Xr_2, Yr_2, 0) = (R_2 \cos(\phi_2), R_1 \sin(\phi_2), 0)$, where $\phi_2$–a tan $2(Ysol_2, Xsol_2)$;

g. the square distance between the two points is $dsq_2 = (Xsol_2 - Xr_2)^2 + (Ysol_2 - Yr_2)^2$ h. update cost function CF+=$dsq_2$;

This is repeated for all M points and minimized using a Levenberg-Marquardt routine as known in the art of the present disclosure to find the optical values of position parameters $t_z^B$, $\theta_{z1}^B$ and $\theta_x^B$, and provide position parameters $t_x^B$ and $t_y^B$.

Still referring to FIGS. 13 and 14A, a stage S96 of flowchart 90 encompasses controller 70 utilizes baseline position parameters $t_x^B$, $t_y^B$, $t_z^B$, $\theta_{z1}^B$ and $\theta_x^B$ and the chirp signal to compute baseline twist parameter $\theta_{z2}^B$.

In one embodiment of stage S96, points on a rim of X-ray ring marker 20 may be parameterized in accordance with the following three equations [2]-[4]:

$$p(t) = R_z^B(\theta_{z1}^B) R_x^B(\theta_x^B) R_z^B(\theta_{z2}^B) \begin{pmatrix} \dfrac{R_i + R_0}{2} \cos(t) \\ \dfrac{R_i + R_0}{2} \sin(t) \\ 0 \end{pmatrix} + \begin{pmatrix} t_x^B \\ t_y^B \\ t_z^B \end{pmatrix}; \quad [2]$$

$$t \in [0, 2\pi]$$

$$p(t) = R_z^B(\theta_{z1}^B)R_x^B(\theta_x^B)R_z^B(\theta_{z2}^B + t)\begin{pmatrix} \frac{R_i + R_0}{2} \\ 0 \\ 0 \end{pmatrix} + \begin{pmatrix} t_x^B \\ t_y^B \\ t_z^B \end{pmatrix}; \quad [3]$$

$$t \in [0, 2\pi]$$

$$p(t_1) = R_z^B(\theta_{z1}^B)R_x^B(\theta_x^B)R_z^B(t_1)\begin{pmatrix} \frac{R_i + R_0}{2} \\ 0 \\ 0 \end{pmatrix} + \begin{pmatrix} t_x^B \\ t_y^B \\ t_z^B \end{pmatrix}; \quad [4]$$

$$t_1 \in [0, 2\pi]$$

Thus, $p(t_1)$ is projected onto the X-ray detector 62 through a perspective transformation with known parameters and the pixel values are retrieved $I(t_1)$ as exemplary shown in FIG. 14A. The chip ring has a model in accordance with the following equation [5]:

$$c(t) = Ae^{jfst(1+tfsh)}; t \in [0,2\pi] \quad [5]$$

where $f_S$ is the start frequency (e.g., 40 Hz) and $f_{sh}$ is the frequency shift (e.g., ½π).

Then, an offset $t_0$ is computed to maximize a normalized cross correlation between signals $I(t_1)$ and $c(t_1+t_0)$. Since the intensity signal embeds the twist $\theta_{z2}^B$ through $t_1$ whereas $c(t)$ doesn't, then $t_0 \equiv \theta_{z2}^B$.

Referring back to FIGS. 11A and 13, a stage S98 of flowchart 90 encompasses controller 70 optimizing baseline position parameters $t_x^B$, $t_y^B$, $t_z^B$, $\theta_{z1}^B$ and $\theta_x^B$ and baseline twist parameter $\theta_{z2}^B$.

In one embodiment of stage S98, a final optimization matches the locations of the object points from the model of the X-ray ring marker 20 with the locations of the object points in the baseline X-ray image 63. This final optimization provides a measure of the Marker Registration Error (MRE) as a squared sum of the distances between the object points projected using the model of the X-ray ring marker 20 and the baseline parameters $t_x^B$, $t_y^B$, $t_z^B$, $\theta_{z1}^B$, $\theta_x^B$ and $\theta_{z2}^B$ the object point projections retrieved from the baseline X-ray image 63. An MRE of less than 1 pixel squared, where a pixel edge length is fixed (e.g., 0.64 mm of a source-detector distance and zoom remained constant across all images), is an indication of an accurate C-Arm→X-ray ring marker registration.

Figure 14B:
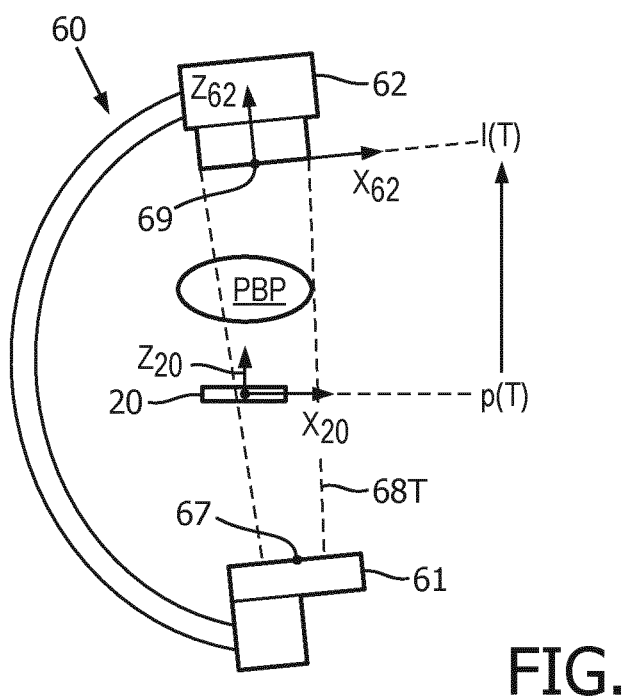
FIG. 14B illustrates an exemplary target imaging pose of a C-Arm in accordance with the various aspects of the present disclosure.

Referring to FIGS. 11B and 12, a stage S86 of flowchart 80 encompasses an acquisition by controller 70 of target X-ray image 64 from C-arm 60 as known in the art of the present disclosure. More particularly, as shown in FIG. 14B, during the target phase the C-Arm→X-ray ring marker registration 71 involves registering a position and a twist of X-ray ring marker 20 of the present disclosure within a target X-ray projection 68T originating from a focal spot 67 of X-ray source 61 to X-ray detector 62.

In practice, a $X_{62}$-$Y_{62}$-$Z_{62}$ coordinate system of C-Arm 60 may be defined on X-ray detector 62 whereby the X-axis and the Y-axis of the coordinate system of C-Arm 60 may be aligned with a coordinate system of the target X-ray image, such as, for example a $X_{65a}$-$Y_{65a}$ coordinate system of target X-ray image 64 shown in FIG. 11B. An origin 69 of $X_{62}$-$Y_{62}$-$Z_{62}$ coordinate system of C-Arm 60 may be delineated whereby X-ray source 62 is on a positive range of a $Z_{62}$ axis of $X_{62}$-$Y_{62}$-$Z_{62}$ coordinate system of C-Arm 60 whereby focal spot 67 of X-ray source 61 has a (0, 0, +$Z_{62}$) coordinate within $X_{62}$-$Y_{62}$-$Z_{62}$ coordinate system of C-Arm 60. Referring back to FIGS. 11B and 12, stage S88 of flowchart 80 encompasses controller 70 deriving target position parameters $t_x^T$, $t_y^T$, $t_z^T$, $\theta_{z1}^T$ and $\theta_x^T$ of X-ray ring marker 20 as a function of an illustration of the centric ring within the target X-ray image 64. The target position parameters $t_x^T$, $t_y^T$, $t_z^T$, $\theta_{z1}^T$ and $\theta_x^T$ are definitive of a position of X-ray ring marker 20 within the target X-ray projection 68B.

Stage S88 of flowchart 80 further encompasses controller 70 deriving a target twist parameter $\theta_{z2}^T$ of X-ray ring marker 20 as a function of the target position parameters $t_x^T$, $t_y^T$, $t_z^T$, $\theta_{z1}^T$ and $\theta_x^T$ and of an illustration of the chirp ring within the target X-ray image 64. The target twist parameter $\theta_{z2}^T$ is definitive of a twist of the X-ray ring marker 20 within the target X-ray projection 68T.

In one embodiment of stage S88, controller 70 executes registration parameter computation method of the present disclosure as represented by flowchart 90 of FIG. 13.

Referring to FIGS. 13 and 14B, stage S92 of flowchart 90 encompasses a computation of a center point 21 of X-ray ring marker 20 on X-ray detector 62.

In one embodiment of stage S92 with spherical objects (e.g., cooper balls or brass balls. etc.), an identification of the spherical objects as illustrated within target X-ray image 64 starts with an adaptive thresholding technique as known in the art of the present disclosure to identify imaging blobs within the target X-ray image 64 followed by a series of morphological operations to eliminate blobs having a smaller size relative to the size of the spherical objects.

From the remaining image blobs within the target X-ray image, image blobs having an aspect ratio close to round and areas between certain thresholds are selected as candidate spherical objects radial pairs whereby blob pairs with a distance therebetween within a certain range are selected as radial pairs whereby an intersection of all lines defined by radial pairs are computed using a least square approach providing a residual. A robustness of identification of the spherical objects as illustrated within a target X-ray image 64 is improved by iteratively eliminating candidate spherical objects that lead to large residual values.

The result of stage S88 is a following listing of an M number of paired objects in the C-Arm coordinate system: $\{[(X_1^1, Y_1^1), (X_1^2, Y_1^2)] \ldots [(X_M^1, Y_M^1), (X_M^2, Y_M^2)]\}$, M≥2.

Still referring to FIGS. 13 and 14B, stage S92 further encompasses controller 70 delineating intersection lines between paired objects $\{[(X_1^1, Y_1^1), (X_1^2, Y_1^2)] \ldots [(X_M^1, Y_M^1), (X_M^2, Y_M^2)]\}$, M≥2, within the target X-ray image 64 to compute a projection $(X_C, Y_C)$ of a center of the X-ray ring marker 20 on the X-ray detector 62.

Referring back to FIGS. 13 and 14B, stage S94 of flowchart 90 encompasses controller 70 utilizing the projection $(X_C, Y_C)$ of a center point 21 of the X-ray ring marker 20 on the X-ray detector 62 during stage S92 to compute target position parameters $t_x^T$, $t_y^T$, $t_z^T$, $\theta_{z1}^T$ and $\theta_x^T$.

In one embodiment of stage S94, based on the projection $(X_C, Y_C)$ of a center point 21 of the X-ray ring marker 20 on the X-ray detector 62, the projection ray defining the center point 21 of the X-ray ring marker 20 extend from source point $(0, 0, S_d^T)$ to detector point $(X_C, Y_C, 0)$. This means that the center point 21 of the X-ray ring marker 20 may be parameterized by the following equation [6]:

$$\begin{pmatrix} t_x^T \\ t_y^T \\ t_z^T \end{pmatrix} = \begin{pmatrix} X_C^T \frac{S_d^T - t_z^T}{S_d^B} \\ Y_C^T \frac{S_d^T - t_z^T}{S_d^T} \\ t_z^T \end{pmatrix}; \quad [6]$$

$$t_z^T \in (0, S_d^T)$$

Assuming the listed landmark points $\{[(X_1^1, Y_1^1), (X_1^2, Y_1^2)] \ldots [(X_M^1, Y_M^1), (X_M^2, Y_M^2)]\}$ is such that the first point belongs to inner centering circle of a radius $R_I$ and the belongs to an the outer centering circle of a radius $R_O$, a cost function may be defined with parameters $t_z^T$, $\theta_{z1}^T$ and $\theta_x^T$ as a measure of how well the object points fit X-ray ring marker 20 placed at a location $(t_x^T, t_y^T, t_z^T)^T$ and angulation $\theta_{z1}^T$ and $\theta_x^T$.

In one embodiment, the cost function is constructed as follows.

First, a cost CF is initialized at a value of zero (0).
Second, for each landmark pair $\{[(X_i^1, Y_i^1), (X_i^2, Y_i^2)]\}$:
  a. a computation of an intersection between segment $\{[(X_i^1, X_i^1, 0), (0, 0, S_d)]\}$ and marker XY plane assuming that the X-ray ring marker 20 is at a location $(t_x^T, t_y^T, t_z^T)^T$ and angulation $\theta_{z1}^T$ and $\theta_x^T$ This point is $(Xsol_1, Ysol_1, 0)$ in the marker coordinate system;
  b. a closest point on the circle to $(xsol_1, ysol_1, 0)$ is $(Xr_1, Yr_1, 0) = (R_1 \cos(\phi_1), R_1 \sin(\phi_1), 0)$, where $\phi_1 = a \tan 2(Ysol_1, Xsol_1)$;
  c. the square distance between the two points is $dsq_1 = (Xsol_1 - Xr_1)^2 + (Ysol_1 - Yr_1)^2$
  d. update cost function $CF += dsq_1$;
  e. a computation of an intersection between segment $\{[(X_i^2, y_i^2, 0), (0, 0, S_d)]\}$ and marker XY plane assuming that the X-ray ring marker 20 is at a location $(t_x^T, t_y^T, t_z^T)^T$ and angulation $\theta_{z1}^T$ and $\theta_x^T$. This point is $(Xsol_2, Ysol_2, 0)$ in the marker coordinate system;
  f. a closest point on the circle to $(Xsol_2, Ysol_2, 0)$ is $(Xr_2, Yr_2, 0) = (R_2 \cos(\phi_2), R_1 \sin(\phi_2), 0)$, where $\phi_2 = a \tan 2(Ysol_2, Xsol_2)$;
  g. the square distance between the two points is $dsq_2 = (Xsol_2 - Xr_2)^2 + (Ysol_2 - Yr_2)^2$
  h. update cost function $CF += dsq_2$;

This is repeated for all M points and minimized using a Levenberg-Marquardt routine as known in the art of the present disclosure to find the optical values of position parameters $t_z^T$, $\theta_{z1}^T$ and $\theta_x^T$, and provide position parameters $t_x^T$ and $t_y^T$.

Still referring to FIGS. 13 and 14B, a stage S96 of flowchart 90 encompasses controller 70 utilizes target position parameters $t_x^T$, $t_y^T$, $t_z^T$, $\theta_{z1}^T$ and $\theta_x^T$ and the chirp signal to compute target twist parameter $\theta_{z2}^T$.

In one embodiment of stage S96, points on a rim of X-ray ring marker 20 may be parameterized in accordance with the following three equations [7]-[9]:

$$p(t) = R_z^T(\theta_{z1}^T) R_x^T(\theta_x^T) R_z^T(\theta_{z2}^T) \begin{pmatrix} \frac{R_i + R_0}{2} \cos(t) \\ \frac{R_i + R_0}{2} \sin(t) \\ 0 \end{pmatrix} + \begin{pmatrix} t_x^T \\ t_y^T \\ t_z^T \end{pmatrix}; \quad [7]$$

$$t \in [0, 2\pi]$$

$$p(t) = R_z^T(\theta_{z1}^T) R_x^T(\theta_x^T) R_z^T(\theta_{z2}^T + t) \begin{pmatrix} \frac{R_i + R_0}{2} \cos(t) \\ \frac{R_i + R_0}{2} \sin(t) \\ 0 \end{pmatrix} + \begin{pmatrix} t_x^T \\ t_y^T \\ t_z^T \end{pmatrix}; \quad [8]$$

$$t \in [0, 2\pi]$$

$$p(t_1) = R_z^T(\theta_{z1}^T) R_x^T(\theta_x^T) R_z^T(t_1) \begin{pmatrix} \frac{R_i + R_0}{2} \cos(t) \\ \frac{R_i + R_0}{2} \sin(t) \\ 0 \end{pmatrix} + \begin{pmatrix} t_x^T \\ t_y^T \\ t_z^T \end{pmatrix}; \quad [9]$$

$$t \in [0, 2\pi]$$

Thus, $p(t_1)$ is projected onto the X-ray detector 62 through a perspective transformation with known parameters and the pixel values are retrieved $I(t_1)$ as exemplary shown in FIG. 14B. The chip ring has a model in accordance with the following equation [10]:

$$c(t) = A e^{jf_s t(1+tf_{sh})}; t \in [0, 2\pi] \quad [10]$$

where $f_S$ is the start frequency (e.g., 40 Hz) and $f_{sh}$ is the frequency shift (e.g., ½π).

Then, an offset $t_0$ is computed to maximize a normalized cross correlation between signals $I(t_1)$ and $c(t_1+t_0)$. Since the intensity signal embeds the twist $\theta_{z2}^T$ through $t_1$ whereas $c(t)$ doesn't, then $t_0 \equiv \theta_{z2}^T$.

Referring back to FIGS. 11B and 13, stage S98 of flowchart 90 encompasses controller 70 optimizing target position parameters $t_x^T$, $t_y^T$, $t_z^T$, $\theta_{z1}^T$ and $\theta_x^T$ and target twist parameter $\theta_{z2}^T$.

In one embodiment of stage S98, a final optimization matches the locations of the object points from the model of the X-ray ring marker 20 with the locations of the object points in the target X-ray image 64. This final optimization provides a measure of the Marker Registration Error (MRE) as a squared sum of the distances between the object points projected using the model of the X-ray ring marker 20 and the target parameters $t_x^T$, $t_y^T$, $t_z^T$, $\theta_{z1}^T$, $\theta_x^T$ and $\theta_{z2}^T$ and the object point projections retrieved from the target X-ray image 64. An MRE of less than 1 pixel squared, where a pixel edge length is fixed (e.g., 0.64 mm of a source-detector distance and zoom remained constant across all images), is an indication of an accurate C-Arm→X-ray ring marker registration.

Referring back to FIG. 12, the generation of the registration parameters via flowchart 100 facilitates an implementation of a wide range of C-Arm intervention technologies including, but not limited to, robot three-dimensional measurements, anatomical/implant tracking, image stitching, pre-operative image overlay and first-time-right C-Arm positioning.

Figure 16:
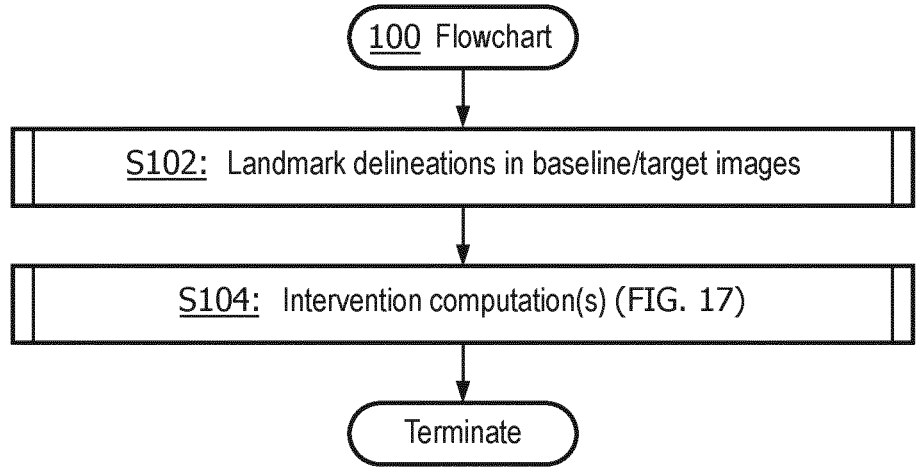
FIG. 16 illustrates a flowchart representative of an exemplary embodiment of a intervention step implementation method in accordance with various aspects of the present disclosure.

Referring to FIG. 16, a flowchart 100 is representative of an intervention step implementation method of the present disclosure in support of such C-Arm intervention technologies.

Figure 18:
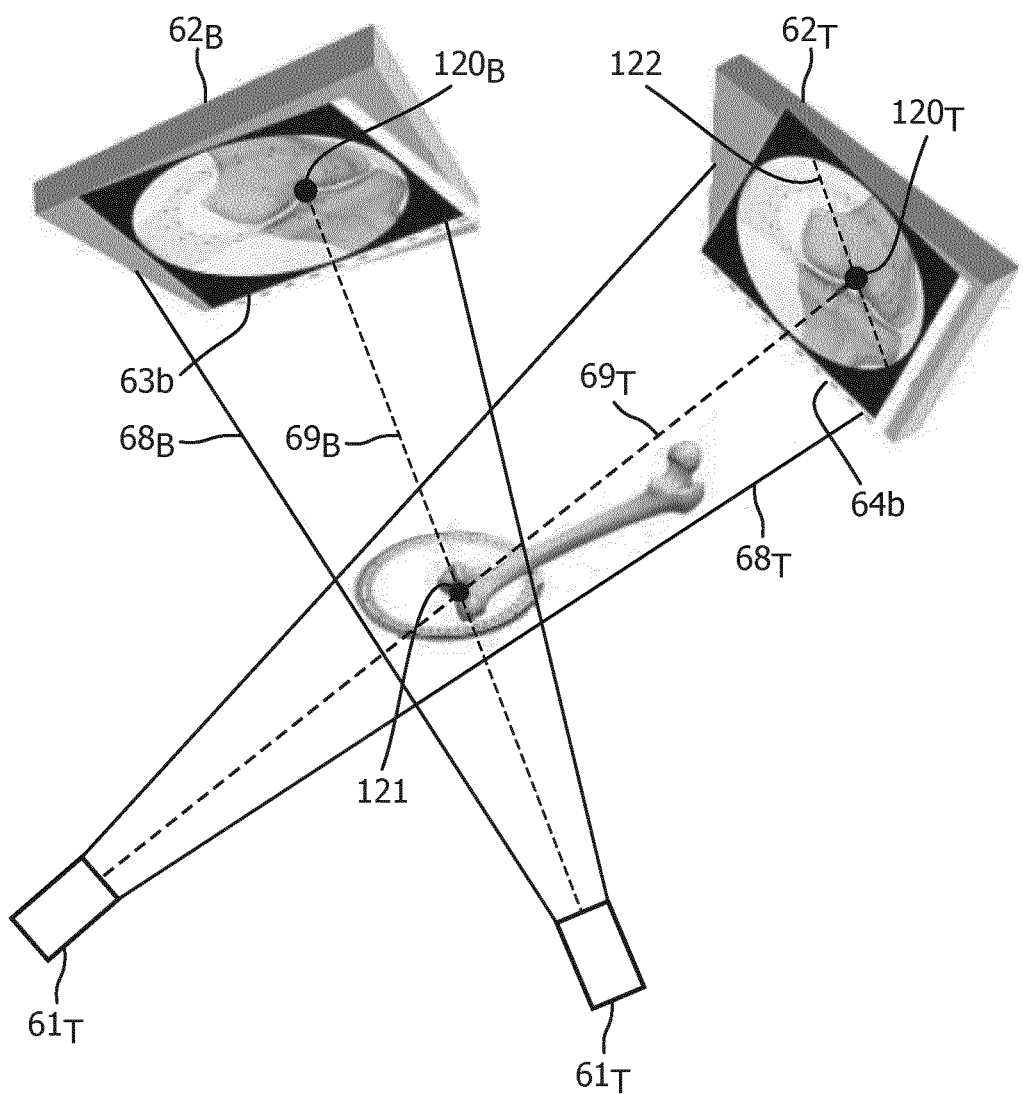
FIG. 18 illustrates an exemplary computation of landmark image delineation of in accordance with various aspects of the present disclosure.
Figure 19:
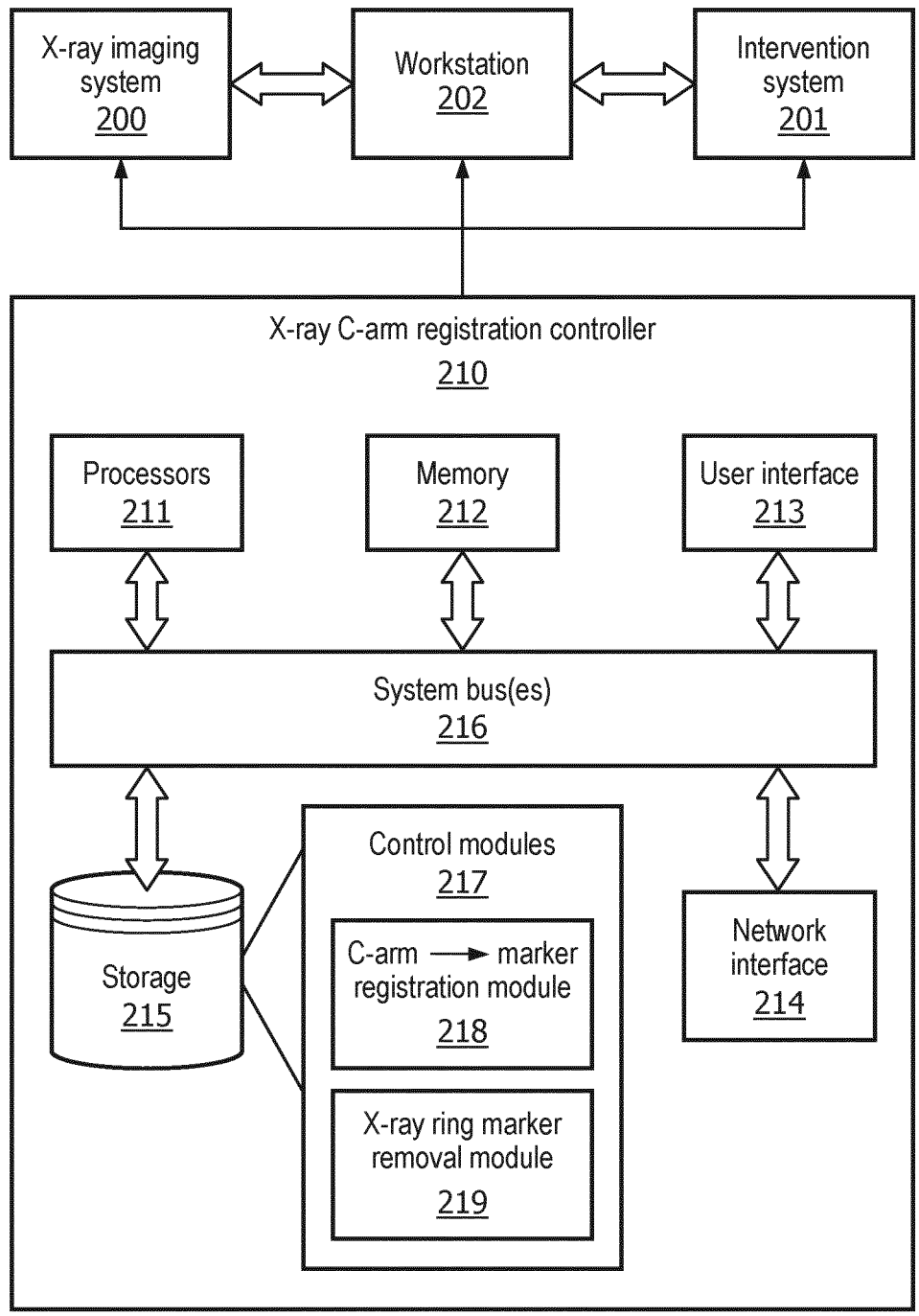
FIG. 19 illustrates an exemplary embodiment of a C-Arm registration controller in accordance with various aspects of the present disclosure.

A stage S102 of flowchart 100 encompasses controller 70 controlling a delineation of a landmark in both the baseline X-ray image and the target X-ray image. For example, as shown in FIG. 18, a point 120$_B$ can be placed on a landmark of a baseline X-ray image 63B via and a projection 122 of this point 120$_B$ may then be overlaid a target X-ray image 64T. The same landmark 120$_T$ can be identified in target X-ray image 64B by sliding the point 120$_T$ along the projection line 122.

Once the same landmark is defined in both images 63B and 64T, controller 70 proceeds to a stage S104 of flowchart 100 to implement an intervention computation, such as, for example, a distance measurement between landmarks in the baseline/target images, a computation of three-dimensional angles between lines in the baseline/target images and three-dimensional reconstruction of linear or tree-like structures from the baseline/target images.

Figure 17:
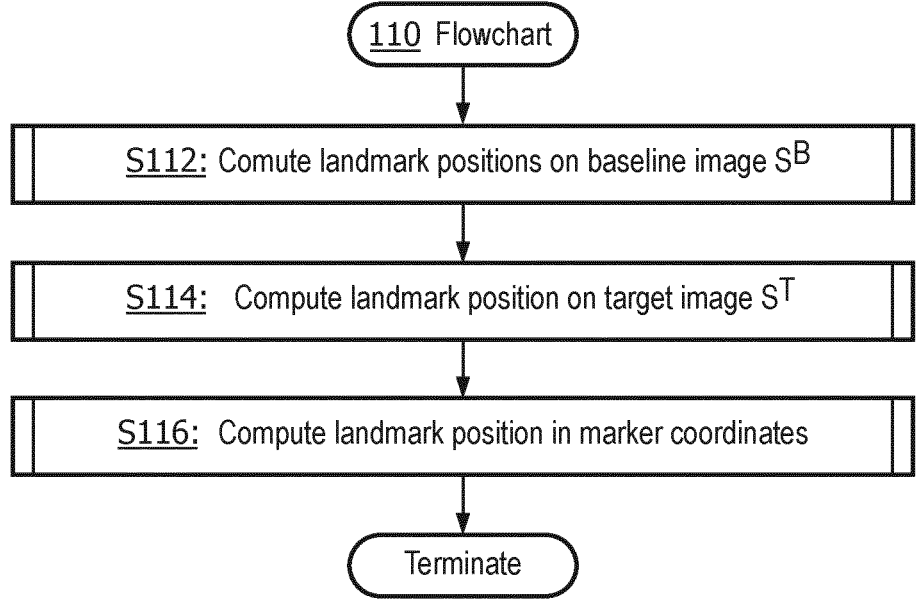
FIG. 17 illustrates a flowchart representative of an exemplary embodiment of a intervention computation method in accordance with various aspects of the present disclosure.

FIG. 17 illustrates a flowchart 110 as one embodiment of stage S104. Flowchart 110 uses the following TABLE 1 of previously computed registration parameters:

TABLE 1

| CArm Position | Registration Parameters | | | | | | Detector Projection | |
|---|---|---|---|---|---|---|---|---|
| | $t_x$ | $t_y$ | $t_z$ | $\theta_{z1}$ | $\theta_x$ | $\theta_{z2}$ | X | Y |
| Baseline | $t_x^B$ | $t_y^B$ | $t_z^B$ | $\theta_{z1}^B$ | $\theta_x^B$ | $\theta_{z2}^B$ | $X^B$ | $Y^B$ |
| Target | $t_x^T$ | $t_y^T$ | $t_z^T$ | $\theta_{z1}^T$ | $\theta_x^T$ | $\theta_{z2}^T$ | $X^T$ | $Y^T$ |

From TABLE 1, homogenous transformations may be computed from marker space to C-Arm space in accordance with the following equations [11] and [12]:

$$H^B = \begin{pmatrix} R_z^B(\theta_{z1}^B) R_x^B(\theta_x^B) R_z^B(\theta_{z2}^B) & \begin{matrix} t_x^B \\ t_y^B \\ t_z^B \end{matrix} \\ 0_{1\times 3} & 1 \end{pmatrix} \quad [11]$$

$$H^T = \begin{pmatrix} R_z^T(\theta_{z1}^T) R_x^T(\theta_x^T) R_z^T(\theta_{z2}^T) & \begin{matrix} t_x^T \\ t_y^T \\ t_z^T \end{matrix} \\ 0_{1\times 3} & 1 \end{pmatrix} \quad [12]$$

where Rz(.) and Rx(.) are 3D rotations around the Z-axis and the A-axis, respectively.

Figure 15:
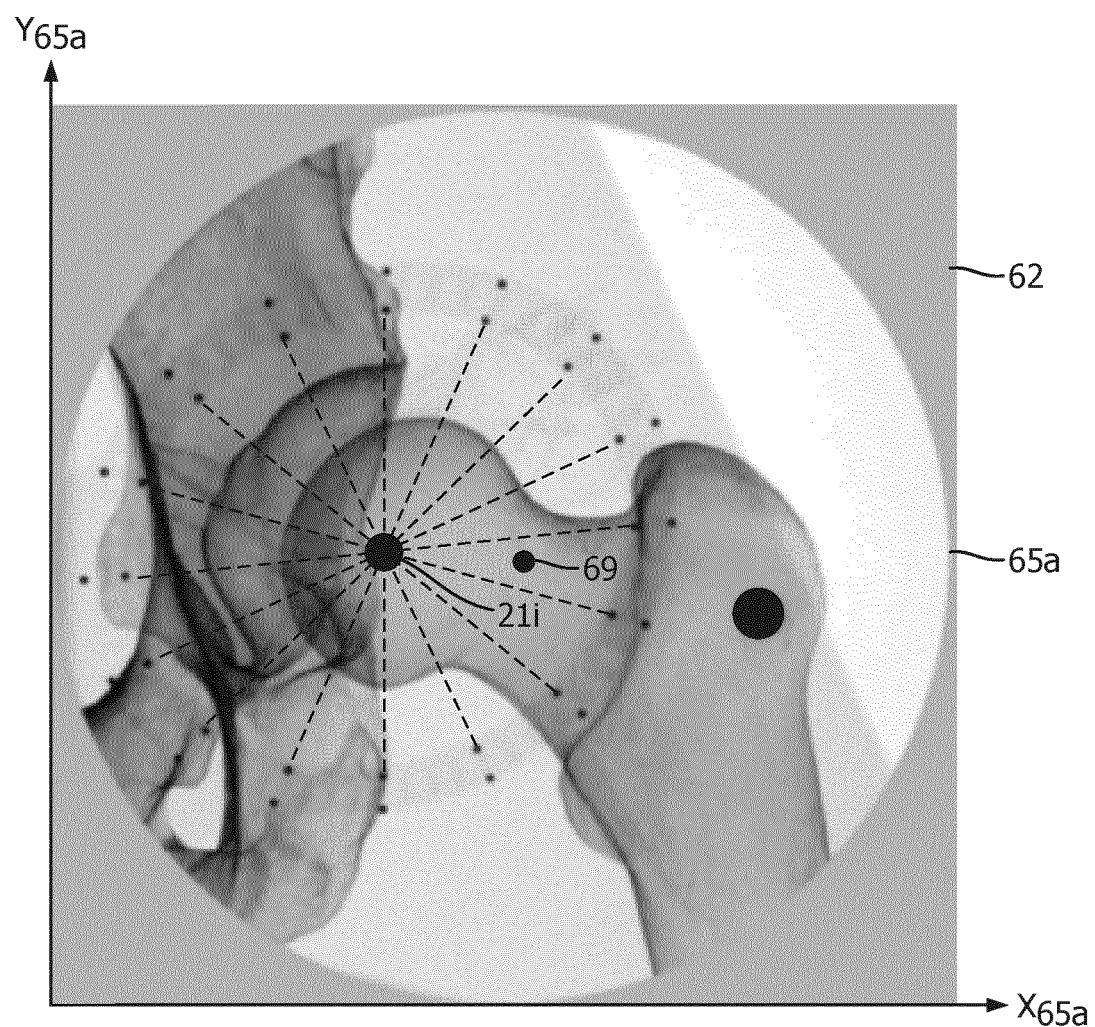
FIG. 15 illustrates an exemplary baseline X-ray image in accordance with the various aspects of the present disclosure.

For the baseline imaging pose, landmark 121 is on ray 69B as shown in FIG. 15 that is defined by points in accordance with the following equations [13] and [14]:

$$S^B = (H^B)^{-1} \begin{pmatrix} 0 \\ 0 \\ S_d^B \\ 1 \end{pmatrix} \quad [13]$$

$$p^B = (H^B)^{-1} \begin{pmatrix} x^B \\ y^B \\ 0 \\ 1 \end{pmatrix} \quad [14]$$

For the target imaging pose, landmark 121 is on ray 69T as shown in FIG. 15 that is defined by points in accordance with the following equations [15] and [16]:

$$S^T = (H^T)^{-1} \begin{pmatrix} 0 \\ 0 \\ S_d^B \\ 1 \end{pmatrix} \quad [15]$$

$$p^T = (H^T)^{-1} \begin{pmatrix} x^T \\ y^T \\ 0 \\ 1 \end{pmatrix} \quad [16]$$

Thus, the 3D position L of the landmark in the marker coordinates is computed by finding the intersection between the $\overline{S^B p^B}$ and $\overline{S^T p^{BT}}$. This embodiment may be extended to multiple points providing 3D landmark positions in marker space. With these it is easy to compute true distances between landmark, 3D angle between lines or to build approximate 3D reconstructions of linear or tree-like structures.

With the two images of the marker in the same position, the controller 70 may perform additional error checking by comparing the distances between known marker landmarks computed from the two views against the ones retrieved from the model.

To facilitate a further understanding of the various inventions of the present disclosure, the following description of FIG. 20 teaches an exemplary embodiment of a C-Arm registration controller of the present disclosure. From this description, those having ordinary skill in the art will appreciate how to apply various aspects of the present disclosure for making and using additional embodiments of C-Arm registration controller of the present disclosure.

Referring to FIG. 20, a C-Arm registration controller 210 includes one or more processor(s) 211, memory 212, a user interface 213, a network interface 214, and a storage 215 interconnected via one or more system buses 216.

Each processor 211 may be any hardware device, as known in the art of the present disclosure or hereinafter conceived, capable of executing instructions stored in memory 212 or storage or otherwise processing data. In a non-limiting example, the processor(s) 211 may include a microprocessor, field programmable gate array (FPGA), application-specific integrated circuit (ASIC), or other similar devices.

The memory 212 may include various memories, as known in the art of the present disclosure or hereinafter conceived, including, but not limited to, L1, L2, or L3 cache or system memory. In a non-limiting example, the memory 212 may include static random access memory (SRAM), dynamic RAM (DRAM), flash memory, read only memory (ROM), or other similar memory devices.

The user interface 213 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 214.

The network interface 214 may include one or more devices, as known in the art of the present disclosure or hereinafter conceived, for enabling communication with other hardware devices. In a non-limiting example, the network interface 214 may include a network interface card (NIC) configured to communicate according to the Ethernet protocol. Additionally, the network interface 214 may implement a TCP/IP stack for communication according to the TCP/IP protocols. Various alternative or additional hardware or configurations for the network interface 214 will be apparent.

The storage 215 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 215 may store instructions for execution by the processor(s) 211 or data upon with the processor(s) 211 may operate. For example, the storage 215 may store a base operating system for controlling various basic operations of the hardware. The storage 215 also stores application modules in the form of executable software/firmware for implementing the various functions of the controller 210 as previously described in the present disclosure including, but not limited to, a C-Arm→X-ray ring marker registration module 218 as an embodiment of C-Arm→X-ray ring marker registration 71 as previously described in the present disclosure, and a ring marker removal module 219 as known in the art of the present disclosure for removing X-ray ring marker from an X-ray image being displayed.

In practice, controller 210 may be installed within a X-ray imaging system 200, an intervention system 201 (e.g., an intervention robot system), or a stand-alone workstation 202 in communication with X-ray imaging 200 system and/or intervention system 201 (e.g., a client workstation or a mobile device like a tablet). Alternatively, components of controller 210 may be distributed among X-ray imaging system 200, intervention system 201 and/or stand-alone workstation 202.

Referring to FIGS. 1-19, those having ordinary skill in the art of the present disclosure will appreciate numerous benefits of the inventions of the present disclosure including, but not limited to, a X-ray ring marker facilitating an accurate and reliable C-Arm Registration, particularly for mobile C-Arms.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of the various and numerous inventions of the present disclosure (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A C-arm registration system, comprising:
a X-ray ring marker including a coaxial construction of a chirp ring and a centric ring on an annular base; and
a C-arm registration controller for registering a C-arm to the X-ray ring marker, wherein the C-arm registration controller is configured to:
acquire a baseline X-ray image illustrative of the X-ray ring marker within a baseline X-ray projection by the C-arm at a baseline imaging pose;
derive baseline position parameters of the X-ray ring marker as a function of an illustration of the centric ring within the baseline X-ray image, the baseline position parameters being definitive of a position of the X-ray ring marker within the baseline X-ray projection; and
derive a baseline twist parameter of the X-ray ring marker as a function of the baseline position parameters and of an illustration of the chirp ring within the baseline X-ray image, the baseline twist parameter being definitive of a twist of the X-ray ring marker within the baseline X-ray projection.

2. The C-arm registration system as claimed in claim 1, wherein the C-arm registration controller being configured to derive the baseline position parameters of the X-ray ring marker includes the C-arm registration controller further configured to:
delineate the centric ring within the baseline X-ray image; and
parameterize the position of the X-ray ring marker within the baseline X-ray projection as a function of a delineation of the centric ring within the baseline X-ray image.

3. The C-arm registration system as claimed in claim 2, wherein the C-arm registration controller being configured to derive the baseline position parameters of the X-ray ring marker includes the C-arm registration controller further configured to:
construct a cost function as a function of a parameterization of the position of the X-ray ring marker within the baseline X-ray projection.

4. The C-arm registration system as claimed in claim 3, wherein the C-arm registration controller being configured to derive the baseline position parameters of the X-ray ring marker includes the C-arm registration controller further configured to:
apply a non-linear least square technique to the cost function.

5. The C-arm registration system as claimed in claim 1, wherein the C-arm registration controller being configured derive the baseline twist parameter includes the C-arm registration controller further configured to:
project points of the X-ray ring marker onto the X-ray detector of the C-arm based on the baseline position parameters; and
parametrize a normalized cross-correlation of a sweep frequency of the chirp ring and image intensity values of the points of the X-ray ring marker projected onto the X-ray detector of the C-arm.

6. The C-arm registration system as claimed in claim 1, wherein the C-arm registration controller is further configured to:
derive a registration error as a function of a location of the centric ring on the X-ray ring marker and a location of the centric ring within the baseline X-ray image.

7. The C-arm registration system as claimed in claim 1, wherein the C-arm registration controller is further configured to:
acquire a target X-ray image illustrative of the X-ray ring marker within a target X-ray projection by the C-arm at a target imaging pose;
derive target position parameters of the X-ray ring marker as a function of an illustration of the centric ring within the baseline X-ray image, the target position parameters being definitive of a position of the X-ray ring marker within the target X-ray projection; and
derive a target twist parameter of the X-ray ring marker as a function of the target position parameters and of an illustration of the chirp ring within the target X-ray image, the target twist parameter being definitive of a twist of the X-ray ring marker within the target X-ray projection.

8. The C-arm registration system as claimed in claim 7, wherein the C-arm registration controller is further configured to:
implement an intervention step based on a landmark as illustrated in the baseline X-ray image and the target X-ray image as a function of the baseline position parameters, the baseline twist parameter, the target position parameters and the target twist parameter.

9. A C-arm registration controller for registering a C-arm to a X-ray ring marker, the X-ray ring marker including a coaxial construction of a chirp ring and a centric ring on an annular base, the C-arm registration controller comprising:
a non-transitory machine-readable storage medium encoded with instructions for execution by at least one processor of a registration of the C-arm to X-ray ring marker, the non-transitory machine-readable storage medium comprising instructions to:
acquire a baseline X-ray image illustrative of the X-ray ring marker within a baseline X-ray projection by the C-arm at a baseline imaging pose;
derive baseline position parameters of the X-ray ring marker as a function of an illustration of the centric ring within the baseline X-ray image, the baseline position parameters being definitive of a position of the X-ray ring marker within the baseline X-ray projection; and
derive a baseline twist parameter of the X-ray ring marker as a function of the baseline position parameters and of an illustration of the chirp ring within the baseline X-ray image, the baseline twist parameter being definitive of a twist of the X-ray ring marker within the baseline X-ray projection.

10. The C-arm registration controller as claimed in claim 9, wherein the instructions to derive the baseline position parameters of the X-ray ring marker includes instructions to:
parameterize the position of the X-ray ring marker within the baseline X-ray projection as a function of a delineation of the centric ring within the baseline X-ray image.

11. The C-arm registration controller as claimed in claim 10, wherein the instructions to derive the baseline position parameters of the X-ray ring marker further includes instructions to:
construct a cost function based on a parameterization of the position of the X-ray ring marker within the baseline X-ray projection.

12. The C-arm registration controller as claimed in claim 9, wherein the instructions to derive the baseline twist parameter of the X-ray ring marker includes instructions to:
project points of the X-ray ring marker onto the X-ray detector of the C-arm based on the baseline position parameters; and
parametrize a normalized cross-correlation of a sweep frequency of the chirp ring and image intensity values of the points of the X-ray ring marker projected onto the X-ray detector of the C-arm.

13. The C-arm registration controller as claimed in claim 9, wherein the non-transitory machine-readable storage medium further comprises instructions to:
derive a registration error as a function of a location of the centric ring on the X-ray ring marker and a location of the centric ring within the baseline X-ray image.

14. The C-arm registration controller as claimed in claim 9, wherein the non-transitory machine-readable storage medium further comprises instructions to:
acquire a target X-ray image illustrative of the X-ray ring marker within a target X-ray projection by the C-arm at a target imaging pose;
derive target position parameters of the X-ray ring marker as a function of an illustration of the centric ring within the baseline X-ray image, the target position parameters being definitive of a position of the X-ray ring marker within the target X-ray projection; and
derive a target twist parameter of the X-ray ring marker as a function of the target position parameters and of an illustration of the chirp ring within the target X-ray image, the target twist parameter being definitive of a twist of the X-ray ring marker within the target X-ray projection.

15. The C-arm registration controller as claimed in claim 14, wherein the non-transitory machine-readable storage medium further comprises instructions to:
implement an intervention step based on a landmark as illustrated in the baseline X-ray image and the target X-ray image as a function of the baseline position parameters, the baseline twist parameter, the target position parameters and the target twist parameter.

16. A C-arm registration method executable by a C-arm registration controller for registering a C-arm to a X-ray ring marker, the X-ray ring marker including a coaxial construction of a chirp ring and a centric ring on an annular base, the C-arm registration method comprising:

acquiring, via the C-arm registration controller, a baseline X-ray image illustrative of the X-ray ring marker within a baseline X-ray projection by the C-arm at a baseline imaging pose;

deriving, via the C-arm registration controller, baseline position parameters of the X-ray ring marker as a function of an illustration of the centric ring within the baseline X-ray image, the baseline position parameters being definitive of a position of the X-ray ring marker within the baseline X-ray projection; and deriving, via the C-arm registration controller, a baseline twist parameter definitive of the X-ray ring marker as a function of the baseline position parameters and of an illustration of the chirp ring within the baseline X-ray image, the baseline twist parameter being definitive of a twist of the X-ray ring marker within the baseline X-ray projection.

17. The C-arm registration method as claimed in claim 16, wherein deriving, via the C-arm registration controller, the baseline position parameters of the X-ray ring marker includes:

parameterizing, via the C-arm registration controller, the position of the X-ray ring marker within the baseline X-ray projection as a function of a delineation of the centric ring within the baseline X-ray image; and constructing, via the C-arm registration controller, a cost function as a function of a parameterization of the position of the X-ray ring marker within the baseline X-ray projection.

18. The C-arm registration method as claimed in claim 17, deriving, via the C-arm registration controller, the baseline twist parameter of the X-ray ring marker includes instructions to:

projecting, via the C-arm registration controller, points of the X-ray ring marker onto the X-ray detector of the C-arm based on the baseline position parameters; and parametrizing, via the C-arm registration controller, a normalized cross-correlation of a sweep frequency of the chirp ring and image intensity values of the points of the X-ray ring marker projected onto the X-ray detector of the C-arm.

19. The C-arm registration method as claimed in claim 16, further comprising:

acquiring, via the C-arm registration controller, a target X-ray image illustrative of the X-ray ring marker within a target X-ray projection by the C-arm at target imaging pose;

deriving, via the C-arm registration controller, target position parameters of the X-ray ring marker as a function of an illustration of the centric ring within the target X-ray image, the target position parameters being definitive of a position of the X-ray ring marker within the target X-ray projection; and deriving, via the C-arm registration controller, a target twist parameter definitive of the X-ray ring marker as a function of the target position parameters and of an illustration of the chirp ring within the target X-ray image, the target twist parameter being definitive of a twist of the X-ray ring marker within the target X-ray projection.

20. The C-arm registration method as claimed in claim 19, further comprising:

implementing, via the C-arm registration controller, an intervention step based on a landmark as illustrated in the baseline X-ray image and the target X-ray image as a function of the baseline position parameters, the baseline twist parameter, the target position parameters and the target twist parameter.

\* \* \* \* \*